(12) United States Patent
Wang et al.

(10) Patent No.: US 12,378,185 B2
(45) Date of Patent: Aug. 5, 2025

(54) N,N-DIHYDROCARBONYLAMIDE CARBOXYLIC ACID, PREPARATION METHOD THEREFOR AND USE THEREOF

(71) Applicant: FUJIAN GOLDEN DRAGON RARE-EARTH Co., Ltd., Longyan (CN)

(72) Inventors: Yanliang Wang, Fujian (CN); Wentao Xiao, Fujian (CN); Yuyuan Wu, Fujian (CN); Jinchi Lin, Fujian (CN)

(73) Assignee: Fujian Golden Dragon Rare-Earth Co., Ltd., Longyan (CN)

( * ) Notice: Subject to any disclaimer, the term of this patent is extended or adjusted under 35 U.S.C. 154(b) by 809 days.

(21) Appl. No.: 17/639,122

(22) PCT Filed: Jun. 24, 2021

(86) PCT No.: PCT/CN2021/102010
§ 371 (c)(1),
(2) Date: Mar. 1, 2022

(87) PCT Pub. No.: WO2022/266919
PCT Pub. Date: Dec. 29, 2022

(65) Prior Publication Data
US 2023/0331662 A1    Oct. 19, 2023

(51) Int. Cl.
C07C 235/76 (2006.01)
C07C 231/02 (2006.01)
(Continued)

(52) U.S. Cl.
CPC .......... *C07C 235/76* (2013.01); *C07C 231/02* (2013.01); *C07C 233/47* (2013.01);
(Continued)

(58) Field of Classification Search
None
See application file for complete search history.

(56) References Cited

U.S. PATENT DOCUMENTS

| 5,786,468 A | 7/1998 | Au et al. |
| 5,844,103 A | 12/1998 | Au et al. |

(Continued)

FOREIGN PATENT DOCUMENTS

| CN | 101945575 A | 1/2011 |
| CN | 103582711 A | 2/2014 |

(Continued)

OTHER PUBLICATIONS

Ajisawa, et al., "Studies on the Synthesis of Cholecystokinin A Receptor Antagonists. II. Synthesis and Cholecystokinin A Receptor Inhibitory Activities of Sulfur-Containing Amide-Carboxylic Acid Derivatives", Yakugaku Zasshi, Dec. 31, 1996, 15 pages with English abstract.

(Continued)

*Primary Examiner* — Amy C Bonaparte
(74) *Attorney, Agent, or Firm* — Pabst Patent Group LLP

(57) ABSTRACT

The present invention provides an N,N-dihydrocarbyl amide carboxylic acid, preparation method therefor and use thereof. The N,N-dihydrocarbyl amide carboxylic acid can be used as an extractant for enriching rare earth elements from raw materials containing low-concentration rare earth elements, separating and purifying yttrium element from mixed rare earth raw material, and separating elements such as aluminum, iron, radioactive thorium, radioactive uranium and actinide from mixed rare earth raw material, etc. The compound can be synthesized in a simple and cost-efficient way. As an extractant, it has good chemical stability and can withstand strong acid and strong alkali without decomposition.

21 Claims, 1 Drawing Sheet

(51) Int. Cl.
*C07C 233/47* (2006.01)
*C07C 233/49* (2006.01)
*C22B 3/32* (2006.01)
*C22B 59/00* (2006.01)

(52) U.S. Cl.
CPC .............. *C07C 233/49* (2013.01); *C22B 3/32* (2021.05); *C22B 59/00* (2013.01)

(56) References Cited

U.S. PATENT DOCUMENTS

2011/0166025 A1* 7/2011 Jentzer ..................... C09D 7/20
   252/364
2014/0234187 A1* 8/2014 Goto ..................... C07C 237/06
   423/21.5

FOREIGN PATENT DOCUMENTS

| | | |
|---|---|---|
| CN | 104529861 A | 4/2015 |
| CN | 106892835 A | 6/2017 |
| CN | 109824532 A | 5/2019 |
| CN | 112575188 A | 3/2021 |
| EP | 0508004 A1 | 10/1992 |
| JP | H03133952 A | 6/1991 |
| JP | H0436266 A | 2/1992 |
| JP | H0495059 A | 3/1992 |

OTHER PUBLICATIONS

Ajisawa, et al., "Studies on the Synthesis of Cholecystokinin A Receptor Antagonists. I. Synthesis and Cholecystokinin A Receptor Inhibitory Activities of Malonamide Derivatives", Yakugaku Zasshi, Dec. 31, 1996, 9 pages with English abstract.
RN 1027464-50-1, Registry Jun. 12, 2008, 1 page.
European Search Report cited in EP21863067.1, mailed Jul. 3, 2023, 9 pages.
International Search Report cited in International Application No. PCT/CN2021/102010 mailed on Dec. 22, 2021, 13 pages.

* cited by examiner

N,N-DIHYDROCARBONYLAMIDE CARBOXYLIC ACID, PREPARATION METHOD THEREFOR AND USE THEREOF

TECHNICAL FIELD

The present invention relates to the technical field of synthesis of organic compounds, in particular to an N,N-dihydrocarbyl amide carboxylic acid, preparation method therefor and use thereof.

BACKGROUND

Rare earth elements refer to 17 metal elements including 15 lanthanides having atomic numbers from 57 to 71 in the periodic table of elements, and scandium with atomic number of 21 and yttrium with atomic number of 39, which have similar chemical properties with lanthanides. Rare earth elements have unique magnetic, optical and electrical properties, and are known as "industrial vitamins". They are widely used in metallurgical industry, petrochemical industry, glass ceramics, energy materials, military industry and other fields, and are important fundamental raw materials for the development of human society.

At present, mining of rare earth minerals in nature comprises steps of: leaching rare earth ions with leaching agent to obtain rare earth leachate, and then extracting and separating rare earth ions one by one through solvent extraction. The development of extractants is the core technology of solvent extraction process, and many factors have to be considered when selecting the extractants for rare earth metals used in industry, such as extraction selectivity, extraction rate, extraction capacity, stability of the compound, solubility, back extraction performance, safety, synthesis method and source, etc. An excellent extractant is one in a million, and a good extractant can simplify production process, improve separation efficiency, reduce production cost and reduce pollution discharge.

Commercially available extractant products known in the field mainly include organic phosphine extractants, carboxylic acid extractants and amine extractants. Typical organic phosphine extractants include phosphonic acid mono(2-ethylhexyl)ester (P507), di(2-ethylhexyl)phosphonic acid (P204), di(2,4,4-trimethylpentyl)phosphinic acid (C272) and tributyl phosphonate(TBP) and the like, the amine extractants include tri-n-octylamine (N235), secondary carbon primary amine (N1923), methyl trioctyl ammonium chloride (N263), and the like, and the carboxylic acid extractants include naphthenic acid, neodecanoic acid, secondary octyl phenoxyacetic acid (CA-12) and the like.

Commercially available extractants still have some shortcomings. For example, P507 is the most widely used extractant in rare earth separation industry, but its separation coefficient for adjacent rare earth elements is low. For example, the separation coefficient for praseodymium and neodymium is only 1.4, which makes it difficult to separate praseodymium and neodymium elements. Naphthenic acid is mainly used to separate and purify yttrium oxide. However, naphthenic acid is a by-product of petrochemical industry, and its composition is complex, so rare earth elements can be extracted under higher pH conditions. After long-term use, its composition is easy to change, which leads to the decrease of organic phase concentration and affects the stability of separation process. CA-12 extractant has been tried to replace naphthenic acid, which can effectively separate yttrium from all lanthanides in the extraction and separation process of rare earth elements and can overcome the problem that the concentration of organic phase decreases when yttrium is extracted and separated by naphthenic acid. However, the separation coefficient for heavy rare earth elements and yttrium in the extraction system is low, which makes it difficult to separate heavy rare earth elements from yttrium, so it is necessary to design more stages of extraction tanks to achieve the separation effect.

Amide carboxylic acid is a new type of extractant containing N and O ligands, and has certain selectivity for the extraction of transition metal ions, stable chemical structure and fast extraction kinetics, thus it is a promising extractant.

The prior art discloses preparation methods of various amide carboxylic acid compounds, for example, CN109824532A discloses a new method for synthesizing N,N,N',N'-tetraoctyl-3-oxopentanediamide (TODGA) comprising the following steps: (1)diglycolic acid reacts with $SOCl_2$ to obtain diglycolyl chloride which then reacts with amine to obtain partial TODGA; (2) water-soluble components are removed from the byproduct, and then monooxamidecarboxylic acid is obtained by separating the product; (3) the monooxamidecarboxylic acid reacts with amine to further obtain part of TODGA. This process combines the characteristics of existing processes and has a high yield.

CN104529861A provides a synthesis method of imide modified low molecular weight line type phenolic resin, which comprises the following steps: in N,N-dimethylformamide or a mixed solvent mainly containing N,N-dimethylformamide, para-aminophenol reacts with anhydride of dicarboxylic acid to obtain an amide carboxylic acid phenolic compound, and then the amide carboxylic acid phenolic compound and 2,6-dimethylol p-cresol undergo polycondensation reaction and dehydration ring closure reaction under the catalysis of acidic catalysts, such as oxalic acid, etc., so as to obtain the imide modified low molecular weight line type phenolic resin.

CN106892835A discloses a bis-diglycidyl amide ligand, a preparation method thereof and a separation and extraction system for lanthanides/actinides containing the bis-diglycidyl amide ligand, wherein the separation and extraction system is formed by mixing an organic phase and aqueous phase in equal volume, and the organic phase contains N,N,N',N',N",N"-hexa-n-octyl nitrilotriacetamide with a molar concentration of 0.1-0.7 mol/L as extractant. N,N,N',N',N",N"-hexa-n-octyl nitrilotriacetamide in the extraction system of this invention has a unique non-N heterocyclic triangular structure, which not only can greatly improve the radiation-resistant of the extraction system, but also does not produce secondary pollutants, which is favorable for the environment. The water-soluble bis-diglycidyl amide ligand is used as masking agent in the extraction system, which is more inclined to complex with the lanthanides, and can effectively mask the lanthanides in the aqueous phase, thus realizing the selective separation of actinides and lanthanides.

From the above, it can be seen that although the prior art provides preparation methods of amide carboxylic acid, it does not provide amide carboxylic acid compounds which can more effectively separate rare earth elements and an extraction separation method thereof. In order to separate rare earth elements more effectively, it is necessary to develop a new extractant having higher separation coefficient compared with the prior art and can overcome the shortcomings in the prior art, and an extraction separation method using thereof.

SUMMARY OF THE INVENTION

To overcome the shortcomings of the prior art, an object of the present invention is to provide an N,N-dihydrocarbyl amide carboxylic acid, preparation method therefor and use thereof. N,N-dihydrocarbyl amide carboxylic acid can be used as an extractant for separating and purifying selected rare earth elements from a mixed rare earth feed liquid, especially for extracting and separating yttrium element from mixed rare earth elements.

In order to achieve the above object, the present invention adopts the following technical solution:

In a first aspect, the present invention provides an N,N-dihydrocarbyl amide carboxylic acid with a structure represented by the following Formula I:

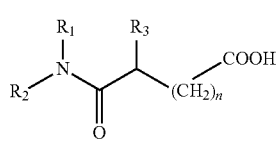

Formula I wherein, $R_1$ and $R_2$ are each independently a linear or branched, saturated or unsaturated, and substituted or unsubstituted C6 or more (for example, C6, C7, C8, C9, C10, C11, C12, C13, C14, C15, C16, C17, C18, C19, C20, C22, C24, C26, C28, C30, C35, C40, etc.) hydrocarbyl;

$R_3$ is a linear or branched, saturated or unsaturated, and substituted or unsubstituted hydrocarbyl;

n is a natural number from 1 to 10 (for example, 1, 2, 3, 4, 5, 6, 7, 8, 9, 10, etc.).

The present invention provides an amide carboxylic acid compound with a structure represented by Formula I as a carboxylic acid extractant for separating rare earth elements and an extraction separation method using the same. This kind of compound has not been reported as extractant for rare earth elements. As a metal extractant, this kind of compound has high separation coefficient for rare earth elements, especially for separating heavy rare earth elements and yttrium element, and can overcome the shortcomings of naphthenic acid in separating yttrium.

Preferably, the hydrocarbyl is any one selected from the group consisting of substituted alkyl, substituted alkenyl and substituted alkynyl, wherein the substituents of the substituted alkyl, the substituted alkenyl and the substituted alkynyl are each independently any one or a combination of at least two selected from the group consisting of halogen, hydroxyl, carboxyl, acyl, ester group, ether group, alkoxy, phenyl, phenoxy, amino, amido, nitro, cyano, mercapto, sulfonyl, thiol, imino, sulfonyl and sulfanyl. Preferably, the substituents are each independently halogen.

Preferably, $R_1$ and $R_2$ are each independently a linear or branched, saturated or unsaturated, and substituted or unsubstituted C6-C30 hydrocarbyl; preferably a linear or branched, saturated or unsaturated, and substituted or unsubstituted C6-C18 hydrocarbyl.

Preferably, $R_1$ and $R_2$ are each independently a linear or branched, saturated or unsaturated, and substituted or unsubstituted C6 or more hydrocarbyl, such as linear or branched, and unsubstituted (C6, C7, C8, C9, C10, C11, C12, C13, C14, C15, C16, C17, C18, C19, C20, C22, C24, C26, C28, C30, C35, C40, etc.) alkyl, alkenyl, alkynyl; preferably a branched, saturated or unsaturated, and unsubstituted C6-C30 hydrocarbyl; more preferably a branched, saturated or unsaturated C6-C10 hydrocarbyl.

Preferably, $R_1$ and $R_2$ are each independently a linear or branched, and unsubstituted C6-C30 alkyl; preferably a linear or branched, and unsubstituted C6-C18 alkyl; and more preferably a linear or branched, and unsubstituted C6-C10 alkyl.

Preferably, n is a natural number from 1 to 6.

Preferably, $R_1$ and $R_2$ are each independently

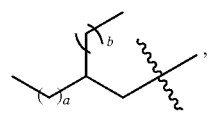

wherein, $2 \leq a+b \leq 10$, ⸝ represents connecting site.

Preferably, $R_1$ and $R_2$ are independently any one selected from the following groups, wherein, ⸝ represent connecting site,

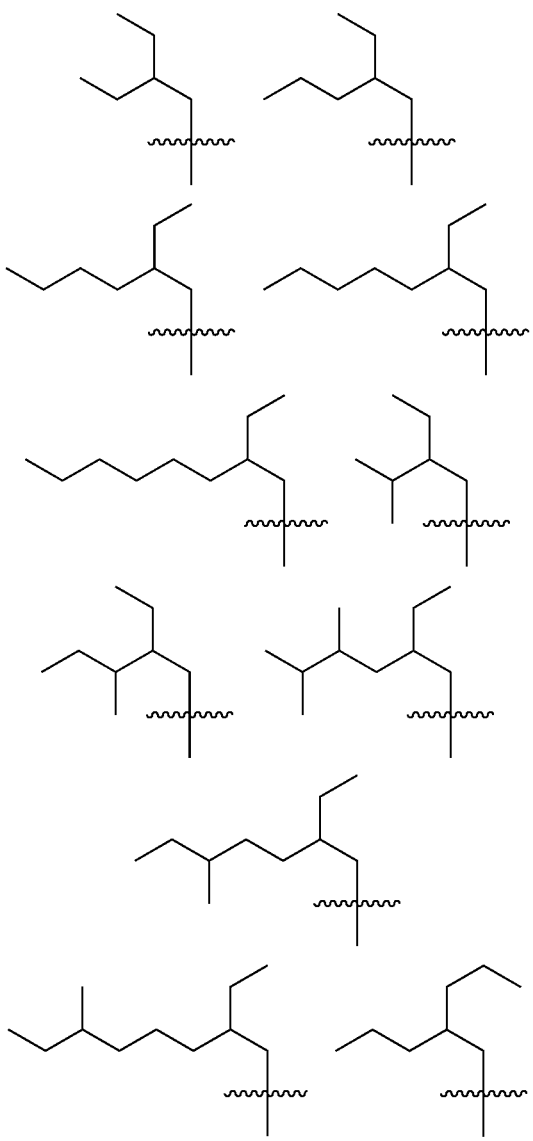

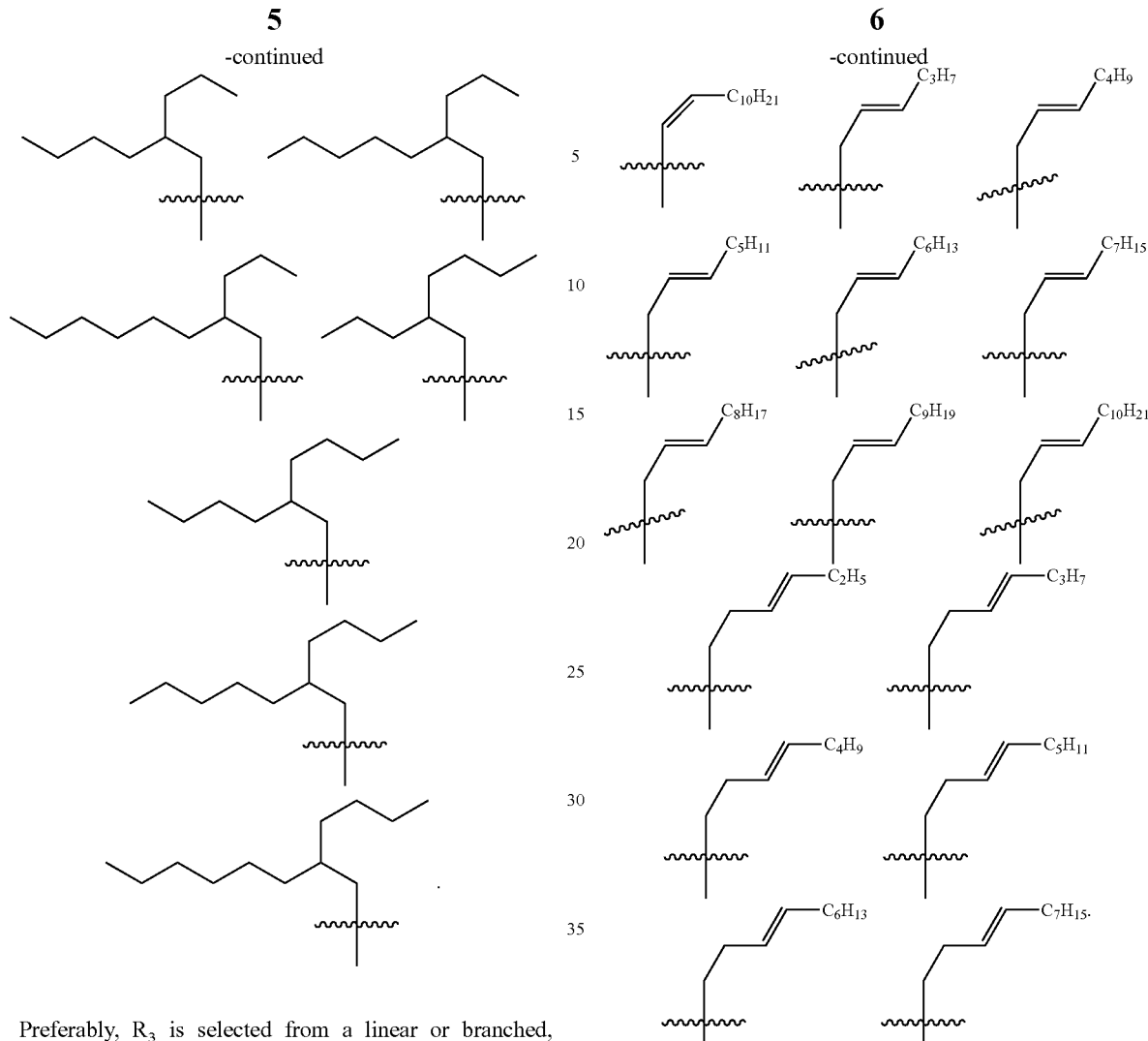

Preferably, $R_3$ is selected from a linear or branched, saturated or unsaturated, and substituted or unsubstituted C6 or more (such as, C6, C7, C8, C9, C10, C11, C12, C13, C14, C15, C16, C17, C18, C19, C20, C30, C40, etc.) hydrocarbyl; preferably a linear or branched, saturated or unsaturated, and substituted or unsubstituted C6-C30 hydrocarbyl.

Preferably, $R_3$ is selected from a linear or branched, unsaturated and unsubstituted C6 or more (such as, C6, C7, C8, C9, C10, C11, C12, C13, C14, C15, C16, C17, C18, C19, C20, etc.) hydrocarbyl; preferably a linear C10 or more alkenyl; and more preferably linear C10-C18 alkenyl.

Preferably, $R_3$ is any one selected from the group consisting of the following groups, wherein  represent connecting site,

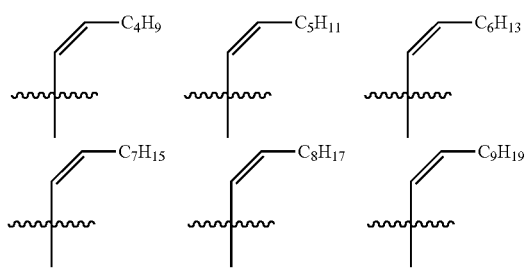

In a second aspect, the present invention provides a method for preparing N,N-dihydrocarbyl amide carboxylic acid according to the first aspect, comprising a step of:

mixing and reacting N,N-dihydrocarbyl secondary amine represented by Formula II and anhydride compound represented by Formula III to obtain N,N-dihydrocarbyl amide carboxylic acid represented by Formula I, as shown in the following Reaction Scheme:

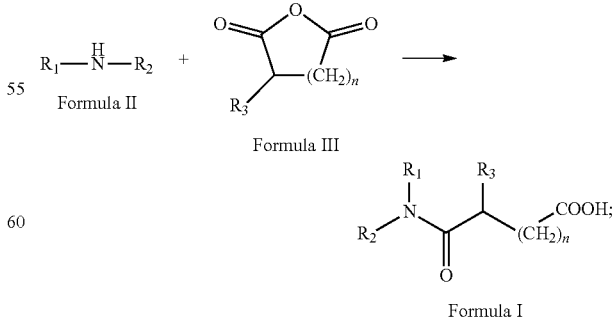

wherein, $R_1$, $R_2$ and $R_3$ are as defined in the first aspect, and n is a natural number from 1 to 10;

Or mixing and reacting N,N-dihydrocarbyl secondary amine represented by Formula II and carboxylic acid monoacyl chloride represented by Formula IV to obtain N,N-dihydrocarbyl amide carboxylic acid represented by Formula I, as shown in the following Reaction Scheme:

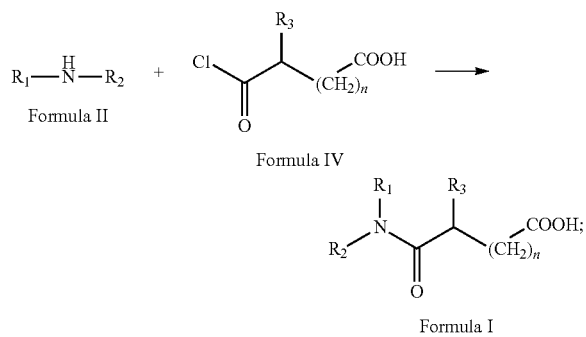

wherein, $R_1$, $R_2$ and $R_3$ are as defined in the first aspect, and n is a natural number from 1 to 10.

Preferably, the molar ratio of N,N-dihydrocarbyl secondary amine represented by Formula II to anhydride compound represented by Formula III is 1:(0.8-1.2). For example, it may be 1:0.8, 1:0.9, 1:1, 1:1.1, 1:1.2, etc.

Preferably, the molar ratio of N,N-dihydrocarbyl secondary amine represented by Formula II to carboxylic acid monoacyl chloride represented by Formula IV is 1:(0.8-1.2). For example, it may be 1:0.8, 1:0.9, 1:1, 1:1.1, 1:1.2, etc.

Preferably, the temperature for mixing and reacting N,N-dihydrocarbyl secondary amine represented by Formula II and anhydride compound represented by Formula III is 0 to 125° C., for example, 0° C., 5° C., 10° C., 15° C., 20° C., 25° C., 30° C., 35° C., 40° C., 50° C., 60° C., 70° C., 80° C., 90° C., 95° C., 100° C., 105° C., 110° C., 115° C., 120° C., 125° C., etc. The mixing and reacting time is 0.5-4 h, for example, 0.5 h, 0.6 h, 0.8 h, 1 h, 1.2 h, 1.4 h, 1.6 h, 1.8 h, 2 h, 2.2 h, 2.4 h, 2.6 h, 2.8 h, 3 h, 3.2 h, 3.4 h, 3.6 h, 3.8 h, 4 h, etc.

Preferably, the temperature of for mixing and reacting N,N-dihydrocarbyl secondary amine represented by Formula II and carboxylic acid monoacyl chloride represented by Formula IV is 0 to 125° C., for example, 0° C., 5° C., 10° C., 15° C., 20° C., 25° C., 30° C., 35° C., 40° C., 50° C., 60° C., 70° C., 80° C., 90° C., 95° C., 100° C., 105° C., 110° C., 115° C., 120° C., 125° C., etc. The mixing and reacting time is 0.5-4 h, for example, 0.5 h, 0.6 h, 0.8 h, 1 h, 1.2 h, 1.4 h, 1.6 h, 1.8 h, 2 h, 2.2 h, 2.4 h, 2.6 h, 2.8 h, 3 h, 3.2 h, 3.4 h, 3.6 h, 3.8 h, 4 h, etc.

Preferably, N,N-dihydrocarbyl secondary amine represented by Formula II and anhydride compound represented by Formula III are mixed and reacted in the absence of a solvent; or in an inert solvent.

Preferably, N,N-dihydrocarbyl secondary amine represented by Formula II and carboxylic acid monoacyl chloride represented by Formula IV are mixed and reacted in the absence of a solvent; or in an inert solvent.

In the present invention, it is worth mentioning that the reaction can also be carried out in the absence of a solvent, and the compound with the structure represented by Formula II and the compound with the structure represented by Formula III are directly mixed and reacted.

Preferably, the inert solvent is selected from any one or a combination of at least two selected from the group consisting of hexane, dichloromethane, petroleum ether, toluene, xylene or kerosene.

In a third aspect, the present invention provides use of the N,N-dihydrocarbyl amide carboxylic acid according to the first aspect in preparing an extractant for separating rare earth elements.

Preferably, the separating rare earth elements specifically refers to extracting and separating yttrium element from a mixture of rare earth elements.

Compared with the prior art, the present invention has the following advantageous effects.

(1) The amide carboxylic acid provided by the present invention can be used for enriching rare earth elements from raw materials containing low-concentration rare earth elements, separating and purifying yttrium element from mixed rare earth raw material, removing elements such as aluminum, iron, radioactive thorium, radioactive uranium and actinide from mixed rare earth raw material, etc., and other fields.

(2) The amide carboxylic acid provided by the present invention has good chemical stability and can withstand strong acid and strong base without decomposition.

BRIEF DESCRIPTION TO THE DRAWING

MODE OF CARRYING OUT THE INVENTION

Figure 1:
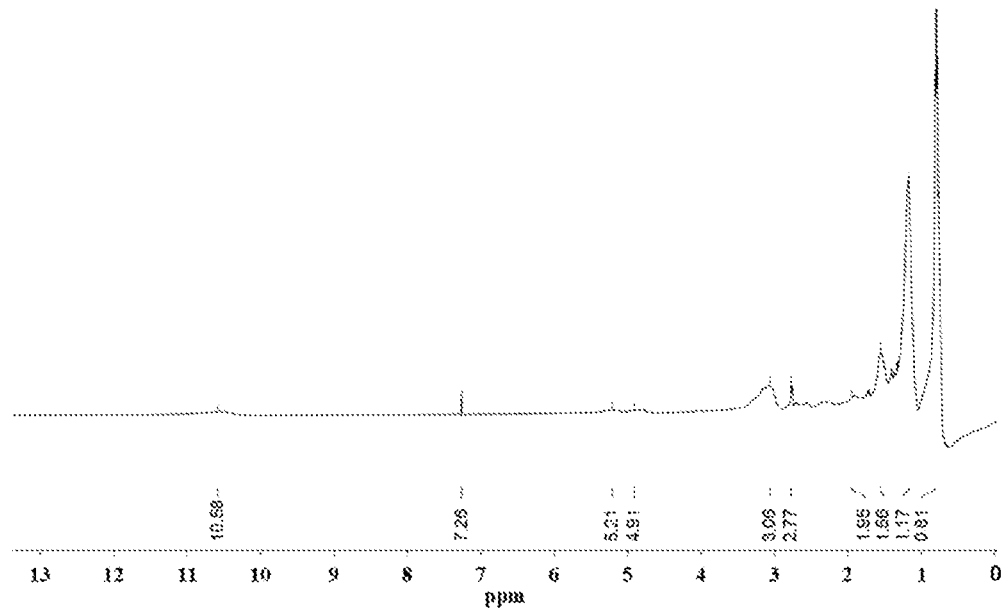
FIG. 1 is a proton nuclear magnetic resonance spectrum of N,N-dihydrocarbyl amide carboxylic acid provided in Example 1.

In the following, the technical solution of the present invention will be further explained with reference to the drawings and specific embodiments. It should be understood to those skilled in the art that the detailed description is intended to aid in the understanding of the present invention, and should not be regarded as a specific limitation of the present invention.

Example 1

The present Example provides a compound I-1 represented by Formula I, which has a structural formula as follows:

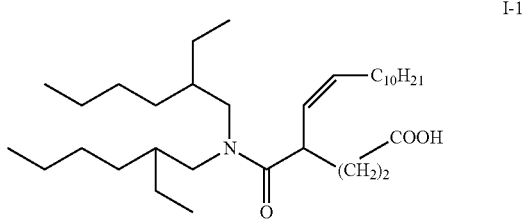

Compound I-1 was prepared by the synthesis route as follows:

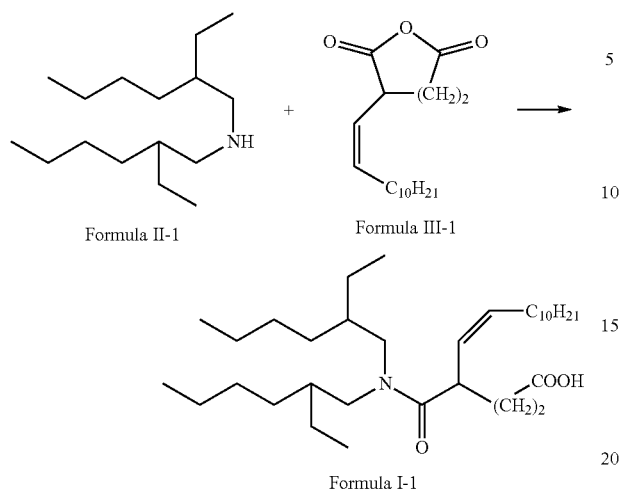

Formula II-1              Formula III-1

Formula I-1

The synthesis method can be carried out with or without a solvent, and the synthesis method with a solvent was as follows:
(1) N,N-diisooctyl secondary amine (24.2 g, 0.10 mol) represented by Formula II-1 was dissolved in toluene (20 mL) to obtain solution 1; dodecenyl glutaric anhydride compound (26.7 g, 0.10 mol) represented by Formula III-1 was dissolved in toluene (30 mL) to obtain solution 2;
(2) the solution 1 was added into the solution 2, the thus obtained mixture was stirred while heating to 80° C. and then kept at 80° C. for two hours. After the reaction was finished, the inert solvent was removed by concentrating in vacuum to obtain the compound I-1.

The synthesis method without a solvent was as follows: N,N-dihydrocarbyl secondary amine represented by Formula II-1 (24.2 g, 0.10 mol) and anhydride represented by Formula III-1 (28.2 g, 0.10 mol) were directly mixed to form a mixed solution, and the mixed solution was stirred while heating to 80° C. and then kept at 80° C. for two hours. After the reaction was finished, the compound I-1 was obtained.

Or N,N-dihydrocarbyl secondary amine represented by Formula II-1 and carboxylic acid-monoacyl chloride compound represented by Formula III-1a were mixed and reacted, as shown in the following Reaction Scheme:

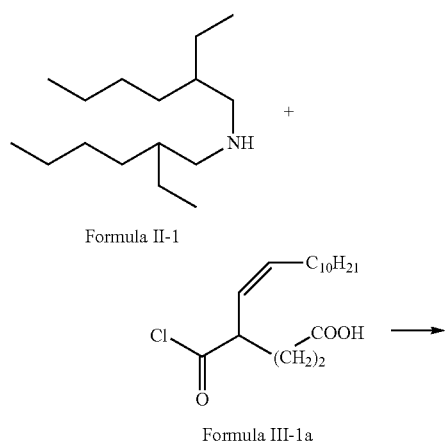

Formula II-1

Formula III-1a

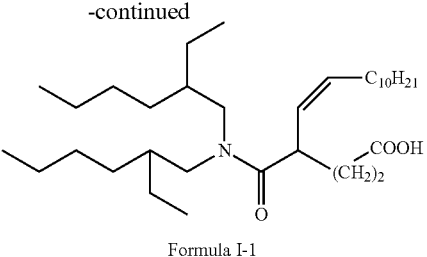

Formula I-1

The synthesis method was as follows: N,N-dihydrocarbyl secondary amine represented by Formula II-1 (24.2 g, 0.10 mol) and carboxylic acid-monochloride compound represented by Formula III-1a (31.7 g, 0.10 mol) were directly mixed to form a mixed solution, and the mixed solution was stirred while heating to 80° C. and then kept at 80° C. for two hours. After the reaction was finished, compound I-1 was obtained.

Figure 2:
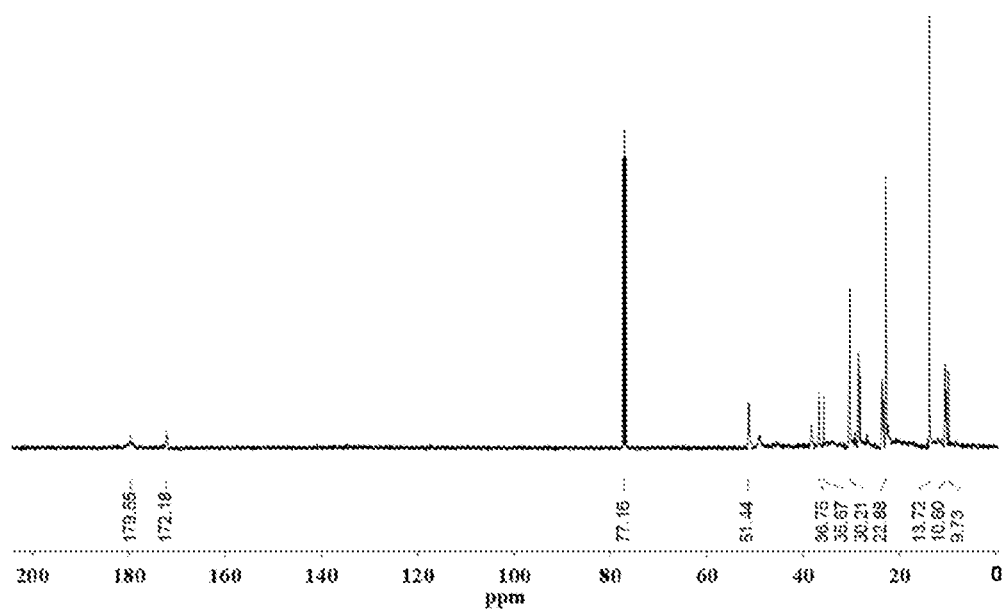
FIG. 2 is a NMR Carbon spectrum of N,N-dihydrocarbyl amide carboxylic acid provided in Example 1.

In the present invention, the compound I-1 was analyzed by nuclear magnetic resonance, and the results were shown in FIGS. 1 and 2.

The analysis of NMR Hydrogen spectrum (FIG. 1) was as follows: $^{1}$H NMR (500 MHz, CDCl$_3$), δ 10.58 (1H), 5.21 (1H), 4.91 (1H), 3.06 (5H), 2.77 (2H), 1.95 (2H), 1.92 (2H), 1.84 (2H), 1.56 (4H), 1.33 (2H), 1.31 (8H), 1.29 (2H), 1.26 (12H), 1.17 (4H), 0.99 (6H), 0.81 (9H).

Among them, peaks at 0.81-1.95 were assigned to hydrogen of alkyl chain in compound I-1; peak at 2.77 was assigned to hydrogen of methylene in

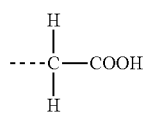

structure; peak at 3.06 was assigned to hydrogen of methylidyne in

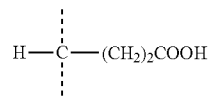

structure and hydrogen of methylene in

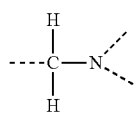

structure; peaks at 4.91 and 5.21 were assigned to two hydrogens of olefin in

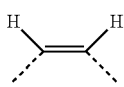

structure; and peak at 10.58 was assigned to hydrogen of carboxyl.

The analysis of NMR carbon spectrum (FIG. 2) was as follows: $^{13}$C NMR (500 MHz, CDCl$_3$), δ 179.5, 172.1, 128.9, 128.3, 51.4 (2C), 36.7 (2C), 35.6, 33.0, 32.0 (2C), 31.9, 29.9, 30.2 (2C), 29.7, 29.7, 29.6, 29.6, 29.3 (2C), 29.3, 27.7, 27.3, 22.8 (2C), 13.7 (2C), 13.7, 10.6 (2C).

Among them, peaks at 10.6-30.2 were assigned to carbon of alkyl chain in compound I-1; peaks at 35.6 and 36.7 were assigned to carbon of methylidyne in the

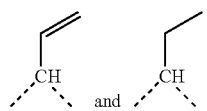

structure; peak at 51.4 was assigned to carbon of methylene in

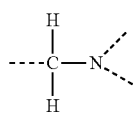

structure; peak at 172.1 was assigned to carbon of amide carbonyl and peak at 179.5 was assigned to carbon of carboxyl.

Example 2

The present Example provides a compound I-2 represented by Formula I, which has a structural Formula as follows:

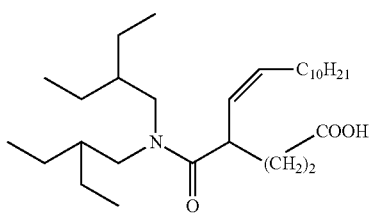

I-2

Compound I-2 was prepared by the synthesis route as follows:

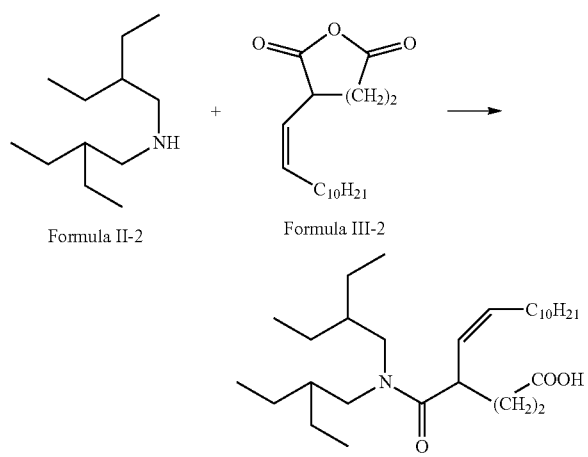

(1) N,N-diisohexyl secondary amine represented by Formula II-2 (18.5 g, 0.10 mol) was dissolved in hexane (20 mL) to obtain solution 1; dodecenyl glutaric anhydride compound represented by Formula III-2 (26.7 g, 0.10 mol) was dissolved in hexane (30 mL) to obtain solution 2;

(2) the solution 1 was added into the solution 2, and the mixed solution was stirred while heating to 80° C. and then kept at 80° C. for two hours. After the reaction was finished, the inert solvent was removed by concentrating in vacuum to obtain compound I-2.

NMR characterization of compound I-2: $^1$H NMR (500 MHz, CDCl$_3$), δ 10.58 (1H), 5.21 (1H), 4.91 (1H), 3.12 (4H), 3.02 (1H), 2.33 (2H), 1.94 (2H), 1.92 (2H), 1.84 (2H), 1.33 (2H), 1.30 (4H), 1.29 (2H), 1.26 (8H), 1.20 (8H), 0.99 (12H), 0.88 (3H).

$^{13}$C NMR (500 MHz, CDCl$_3$), δ 178.4, 170.8, 128.9, 128.3, 52.1 (2C), 39.7 (2C), 37.4, 33.0, 31.9, 29.9, 29.7, 29.7, 29.6, 29.6, 29.3, 27.7, 27.3, 25.7 (4C), 22.7, 14.1, 11.6 (4C).

Example 3

The present Example provides a compound I-3 represented by Formula I, which has a structural Formula as follows:

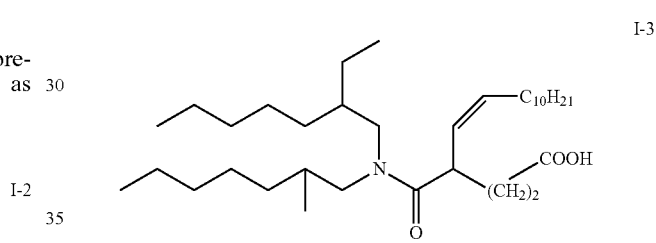

I-3

Compound I-3 was prepared by the synthesis route as follows:

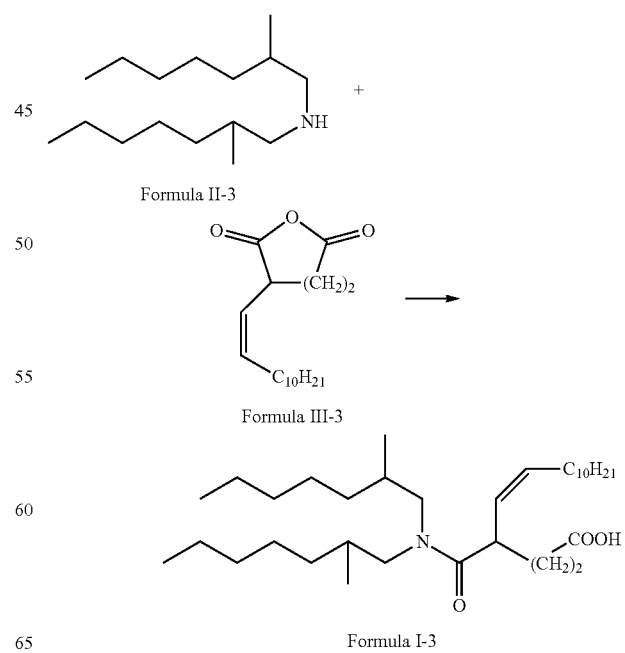

13

(1) N,N-dihydrocarbyl secondary amine represented by Formula II-3 (24.2 g, 0.10 mol) was dissolved in petroleum ether (20 mL) to obtain solution 1; dodecenyl glutaric anhydride compound represented by Formula III-3 (28.2 g, 0.10 mol) was dissolved in petroleum ether (30 mL) to obtain solution 2;
(2) the solution 1 was added into the solution 2, and the thus obtained mixture was stirred while heating to 80° C. and then kept at 80° C. for two hours. After the reaction was finished, the inert solvent was removed by concentrating in vacuum to obtain compound I-3.

NMR characterization of compound I-3: $^1$H NMR (500 MHz, CDCl$_3$), δ 10.58 (1H), 5.21 (1H), 4.91 (1H), 3.25 (4H), 3.02 (1H), 2.37 (2H), 2.12 (2H), 1.94 (2H), 1.85 (2H), 1.33 (2H), 1.30 (4H), 1.29 (2H), 1.28 (4H), 1.26 (8H), 1.25 (4H), 1.24 (4H), 1.19 (4H), 0.93 (6H), 0.88 (6H), 0.87 (3H).
$^{13}$C NMR (500 MHz, CDCl$_3$), δ 178.5, 170.1, 128.7, 128.1, 54.4 (2C), 37.4, 34.8 (2C), 33.0, 32.1 (2C), 31.9, 30.8 (2C), 29.9, 29.7, 29.7, 29.6, 29.6, 29.3, 27.7, 27.3, 26.5 (2C), 22.7 (2C), 22.7, 18.4 (2C), 14.1 (2C), 14.0.

Example 4

The present Example provides a compound I-4 represented by Formula I, which has a structural Formula as follows:

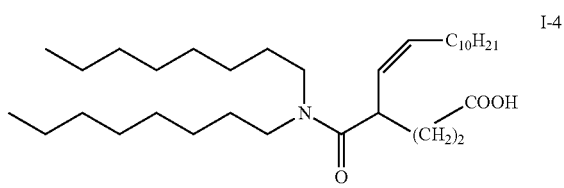

Compound I-4 was prepared by the synthesis route as follows:

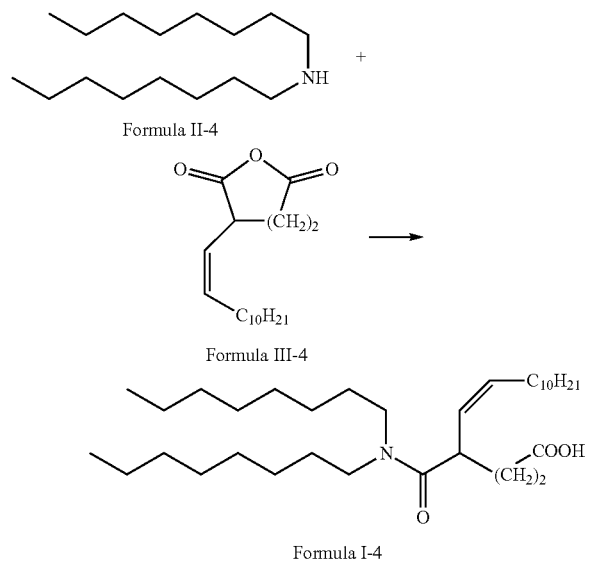

(1) N,N-dihydrocarbyl secondary amine represented by Formula II-4 (24.2 g, 0.10 mol) was dissolved in toluene (20 mL) to obtain solution 1; dodecenyl glutaric anhydride compound represented by Formula III-4 (28.2 g, 0.10 mol) was dissolved in toluene (30 mL) to obtain solution 2;

14

(2) the solution 1 was added into the solution 2, and the mixed solution was stirred while heating to 80° C. and then kept at 80° C. for two hours. After the reaction was finished, toluene was removed by concentrating in vacuum to obtain compound I-4.

NMR characterization of compound I-4: $^1$H NMR (500 MHz, CDCl$_3$), δ 10.58 (1H), 5.21 (1H), 4.91 (1H), 3.18 (4H), 3.02 (1H), 2.33 (2H), 1.94 (2H), 1.84 (2H), 1.52 (4H), 1.33 (2H), 1.30 (2H), 1.30 (2H), 1.29 (2H), 1.29 (4H), 1.27 (4H), 1.26 (8H), 1.26 (4H), 1.26 (4H), 1.26 (4H), 0.88 (9H).
$^{13}$C NMR (500 MHz, CDCl$_3$), δ 178.4, 170.8, 128.9, 128.3, 50.0 (2C), 37.4, 33.0, 31.9 (2C), 31.9, 29.9, 29.7, 29.7, 29.6, 29.6, 29.3, 29.3 (2C), 29.3 (2C), 29.3 (2C), 27.0 (2C), 22.7 (2C), 27.7, 27.3, 22.7, 14.1 (2C), 14.1.

Example 5

The present Example provides a compound I-5 represented by Formula I, which has a structural Formula as follows:

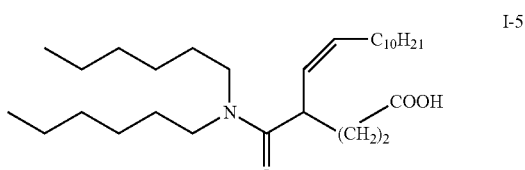

Compound I-5 was prepared by the synthesis route as follows:

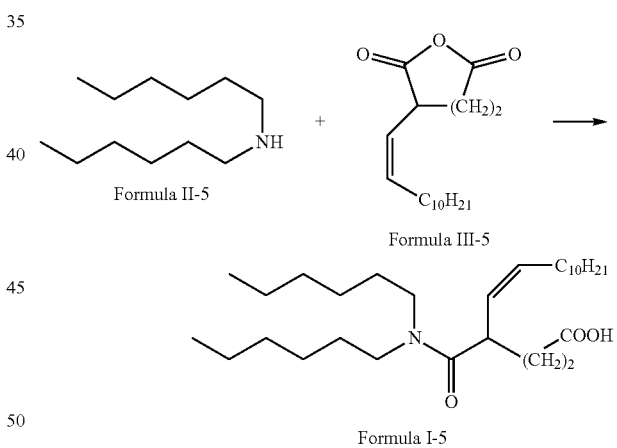

(1) N,N-dihydrocarbyl secondary amine represented by Formula II-5 (18.6 g, 0.10 mol) was dissolved in toluene (20 mL) to obtain solution 1; dodecenyl glutaric anhydride compound represented by Formula III-5 (28.0 g, 0.10 mol) was dissolved in toluene (30 mL) to obtain solution 2;
(2) the solution 1 was added into the solution 2, and the thus obtained mixture was stirred while heating to 80° C. and then kept at 80° C. for two hours. After the reaction was finished, toluene was removed by concentrating in vacuum to obtain compound I-5.

NMR characterization of compound I-5: $^1$H NMR (500 MHz, CDCl$_3$), δ 10.58 (1H), 5.21 (1H), 4.91 (1H), 3.18 (4H), 3.02 (1H), 2.33 (2H), 1.94 (2H), 1.84 (2H), 1.52 (4H), 1.33 (2H), 1.30 (2H), 1.30 (2H), 1.29 (2H), 1.29 (4H), 1.28 (4H), 1.28 (4H), 1.26 (8H), 0.88 (3H), 0.88 (6H).

$^{13}$C NMR (500 MHz, CDCl$_3$), δ 178.4, 170.8, 128.9, 128.3, 50.0 (2C), 37.4, 33.0, 31.9, 31.5 (2C), 29.9, 29.7, 29.7, 29.6, 29.6, 29.3, 29.3 (2C), 27.7, 27.3, 26.7 (2C), 22.7 (2C), 22.7, 14.1 (2C), 14.1.

Example 6

The present Example provides a compound I-6 represented by Formula I, which has a structural Formula as follows:

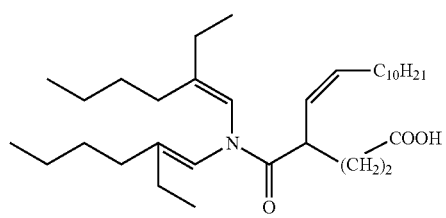

Formula I-6

Compound I-6 was prepared by the synthesis route as follows:

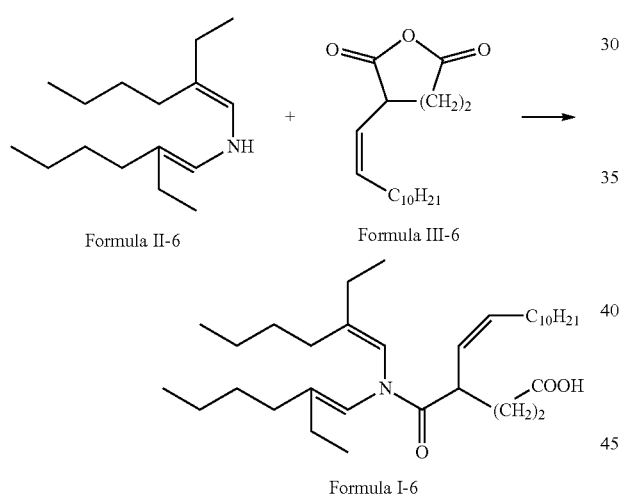

Formula II-6    Formula III-6

Formula I-6

(1) N,N-dihydrocarbyl secondary amine represented by Formula II-6 (23.8 g, 0.10 mol) was dissolved in toluene (20 mL) to obtain solution 1; dodecenyl glutaric anhydride compound represented by Formula III-6 (26.7 g, 0.10 mol) was dissolved in toluene (30 mL) to obtain solution 2;

(2) the solution 1 was added into the solution 2, and the thus obtained mixture was stirred while heating to 80° C. and then kept at 80° C. for two hours. After the reaction was finished, toluene was removed by concentrating in vacuum to obtain compound I-6.

NMR characterization of compound I-6: $^1$H NMR (500 MHz, CDCl$_3$), δ 10.58 (1H), 6.83 (2H), 5.21 (1H), 4.91 (1H), 3.02 (1H), 2.33 (2H), 2.18 (4H), 2.0 (4H), 1.94 (2H), 1.84 (2H), 1.33 (2H), 1.38 (4H), 1.30 (2H), 1.30 (2H), 1.29 (2H), 1.29 (4H), 1.26 (8H), 0.93 (6H), 0.88 (3H), 0.85 (6H).

$^{13}$C NMR (500 MHz, CDCl$_3$), δ 178.4, 165.7, 128.9, 128.3, 124.6 (2C), 116.6 (2C), 37.6, 33.0, 31.9, 29.9, 29.7, 29.7, 29.6, 29.6, 29.6 (2C), 29.3, 28.0 (2C), 27.9, 27.7 (2C), 27.3, 23.1 (2C), 22.7, 14.2 (2C), 14.1, 11.8 (2C).

Example 7

The present Example provides a compound I-7 represented by Formula I, which has a structural Formula as follows:

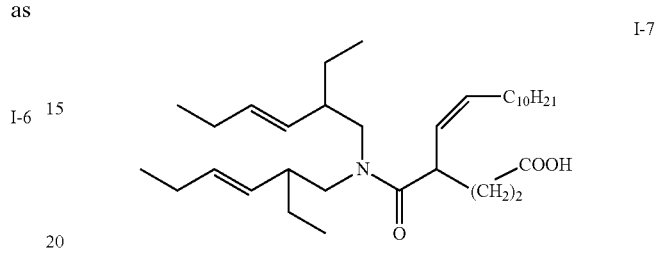

Compound I-7 was prepared by the synthesis route as follows:

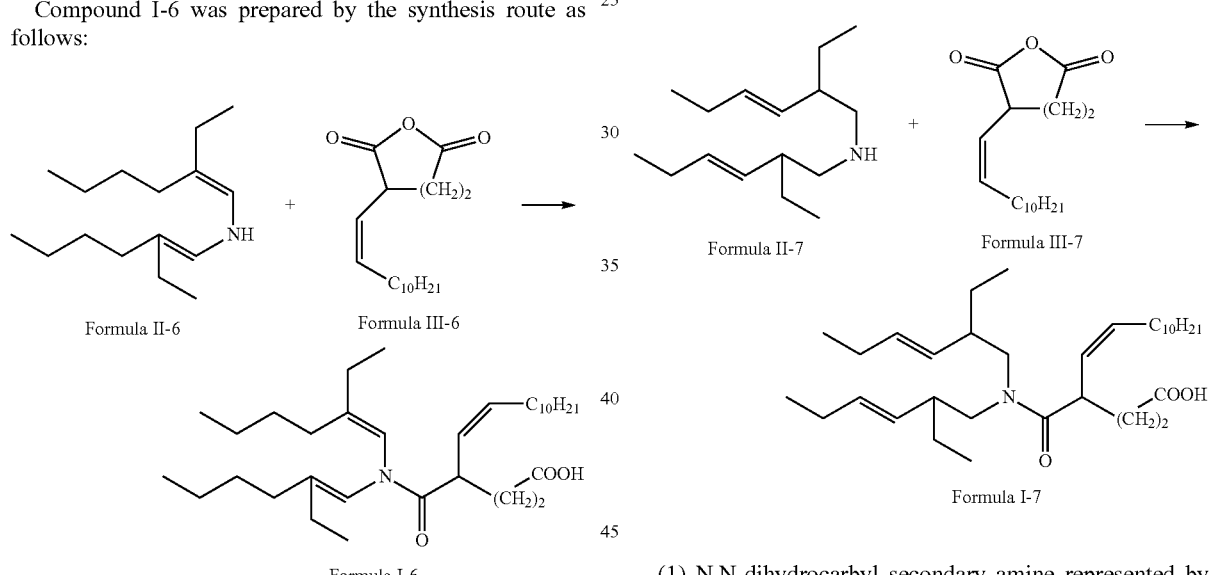

Formula II-7    Formula III-7

Formula I-7

(1) N,N-dihydrocarbyl secondary amine represented by Formula II-7 (23.7 g, 0.10 mol) was dissolved in toluene (20 mL) to obtain solution 1; anhydride compound represented by Formula III-7 (28.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hours. After the reaction was finished, toluene was removed by concentrating in vacuum to obtain compound I-7.

NMR characterization of compound I-7: $^1$H NMR (500 MHz, CDCl$_3$), δ 10.58 (1H), 5.48 (2H), 5.43 (2H), 5.21 (1H), 4.91 (1H), 3.31 (4H), 3.02 (1H), 2.70 (2H), 2.33 (2H), 2.0 (4H), 1.94 (2H), 1.84 (2H), 1.44 (4H), 1.33 (2H), 1.30 (2H), 1.30 (2H), 1.29 (2H), 1.26 (8H), 0.94 (6H), 0.88 (3H), 0.79 (6H).

$^{13}$C NMR (500 MHz, CDCl$_3$), δ 178.4, 170.8, 135.6 (2C), 129.3 (2C), 128.9, 128.3, 55.5 (2C), 39.9 (2C), 37.4, 33.0, 31.9, 29.9, 29.7, 29.7, 29.6, 29.6, 29.3, 27.7, 27.3, 26.8 (2C), 26.7 (2C), 22.7, 14.3 (2C), 14.1, 11.7 (2C).

Example 8

The present Example provides a compound I-8 represented by Formula I, which has a structural Formula as follows:

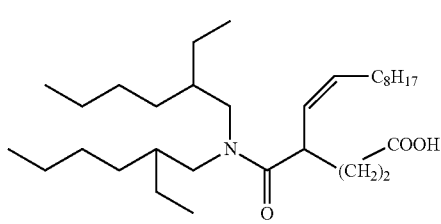

Compound I-8 was prepared by the synthesis route as follows:

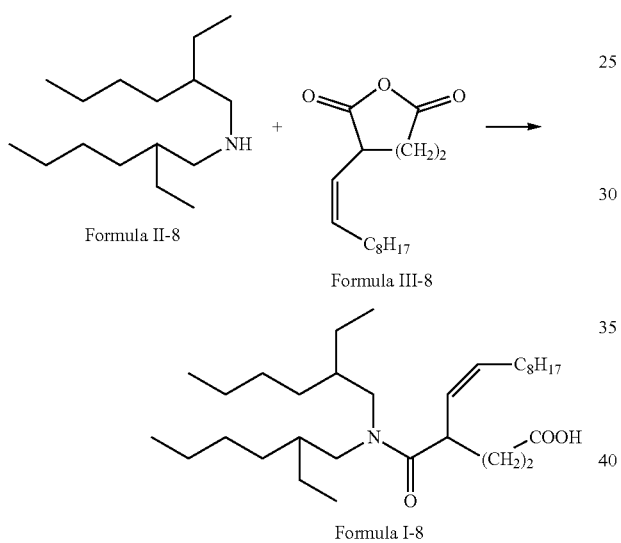

(1) N,N-dihydrocarbyl secondary amine represented by Formula II-8 (24.2 g, 0.10 mol) was dissolved in toluene (20 mL) to obtain solution 1; decenyl glutaric anhydride compound represented by Formula III-8 (25.4 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hours. After the reaction was finished, toluene was removed by concentrating in vacuum to obtain compound I-8.

NMR characterization of compound I-8: $^1$H NMR (500 MHz, CDCl$_3$), δ 10.58 (1H), 5.21 (1H), 4.91 (1H), 3.25 (4H), 3.02 (1H), 2.33 (2H), 1.94 (2H), 1.92 (2H), 1.84 (2H), 1.55 (4H), 1.33 (2H), 1.31 (4H), 1.30 (2H), 1.29 (2H), 1.26 (6H), 1.25 (4H), 1.19 (4H), 0.99 (4H), 0.88 (6H), 0.88 (3H).

$^{13}$C NMR (500 MHz, CDCl$_3$), δ 178.4, 170.8, 128.9, 128.3, 52.4 (2C), 37.5 (2C), 37.4, 33.0, 32.0 (2C), 31.9, 29.9, 29.8 (2C), 29.7, 29.7, 29.3 (2C), 29.3, 27.7, 27.3, 23.0 (2C), 22.7, 14.1 (2C), 14.1, 11.6 (2C).

Example 9

The present Example provides a compound I-9 represented by Formula I, which has a structural Formula as follows:

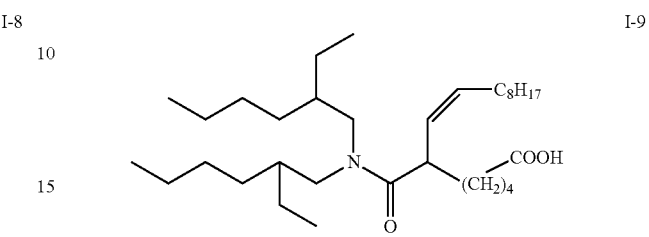

Compound I-9 was prepared by the synthesis route as follows:

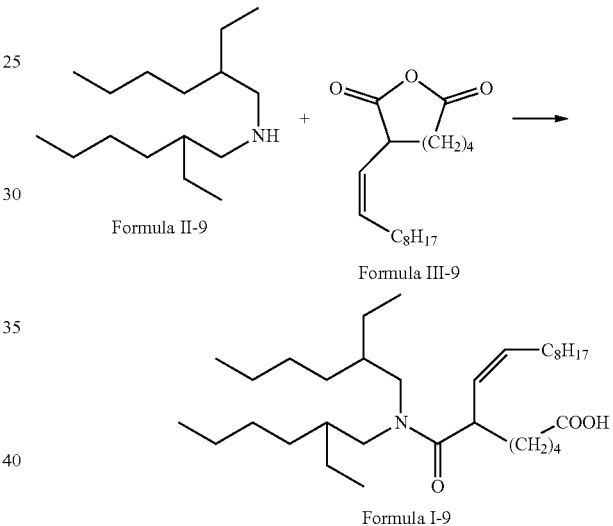

(1) N,N-dihydrocarbyl secondary amine represented by Formula II-9 (24.2 g, 0.10 mol) was dissolved in toluene (20 mL) to obtain solution 1; decenyl pimelic anhydride compound represented by Formula III-9 (28.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hours. After the reaction was finished, toluene was removed by concentrating in vacuum to obtain compound I-9.

NMR characterization of compound I-9: $^1$H NMR (500 MHz, CDCl$_3$), δ 10.43 (1H), 5.21 (1H), 4.91 (1H), 3.25 (4H), 3.02 (1H), 2.21 (2H), 1.94 (2H), 1.92 (2H), 1.55 (2H), 1.55 (4H), 1.54 (2H), 1.33 (2H), 1.31 (4H), 1.30 (2H), 1.30 (2H), 1.29 (2H), 1.26 (8H), 1.25 (1H), 1.25 (4H), 1.19 (4H), 0.99 (6H), 0.88 (6H), 0.88 (3H).

$^{13}$C NMR (500 MHz, CDCl$_3$), δ 178.4, 170.8, 130.9, 128.8, 52.4 (2C), 38.0, 37.5 (2C), 34.5, 34.0, 32.0 (2C), 31.9, 29.9, 29.8 (2C), 29.7, 29.7, 29.6, 29.6, 29.3, 29.3 (2C), 27.3, 25.9, 24.4, 23.0 (2C), 22.7, 14.1 (2C), 14.1, 11.6 (2C).

Example 10

The present Example provides a compound I-10 represented by Formula I, which has a structural Formula as follows:

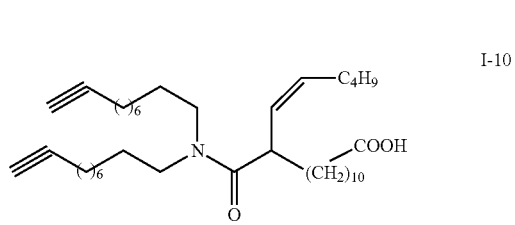

I-10

Compound I-10 was prepared by the synthesis route as follows:

Formula II-10 + Formula III-10 → Formula I-10

(1) N,N-dihydrocarbyl secondary amine represented by Formula II-10 (29.4 g, 0.10 mol) was dissolved in toluene (20 mL) to obtain solution 1; decenyl pimelic anhydride compound represented by Formula III-10 (30.8 g, 0.10 mol) was dissolved in toluene (30 mL) to obtain solution 2;

(2) the solution 1 was added into the solution 2, and the mixed solution was stirred while heating to 80° C. and then kept at 80° C. for two hours. After the reaction was finished, toluene was removed by concentrating in vacuum to obtain compound I-10.

NMR characterization of compound I-10: $^1$H NMR (500 MHz, CDCl$_3$), δ 10.18 (1H), 5.21 (1H), 4.91 (1H), 3.18 (4H), 3.02 (1H), 2.87 (2H), 2.46 (4H), 2.21 (2H), 1.94 (2H), 1.55 (2H), 1.54 (2H), 1.52 (4H), 1.44 (4H), 1.38 (2H), 1.33 (2H), 1.30 (2H), 1.29 (4H), 1.29 (4H), 1.29 (4H), 1.27 (4H), 1.26 (2H), 1.26 (2H), 1.26 (2H), 1.26 (4H), 1.25 (2H), 1.25 (2H), 1.29 (2H), 0.93 (3H).

$^{13}$C NMR (500 MHz, CDCl$_3$), δ 178.4, 170.8, 128.9, 130.9, 83.7 (2C), 68.6 (2C), 50.0 (2C), 38.0, 34.8, 34.0, 32.1, 29.9, 29.6, 29.6, 29.6, 29.3, 29.3, 29.3 (2C), 29.3 (2C), 29.0, 28.7 (2C), 28.7 (2C), 28.4 (2C), 27.0, 27.0 (2C), 24.7, 22.8, 18.4 (2C), 14.2.

Example 11

The present Example provides a compound I-11 represented by Formula I, which has a structural Formula as follows:

I-11

Compound I-11 was prepared by the synthesis route as follows:

Formula II-11 + Formula III-11 → Formula I-11

(1) N,N-dihydrocarbyl secondary amine represented by Formula II-11 (51.3 g, 0.10 mol) was dissolved in toluene (20 mL) to obtain solution 1; decenyl pimelic anhydride compound represented by Formula III-11 (42.0 g, 0.10 mol) was dissolved in toluene (30 mL) to obtain solution 2;

(2) the solution 1 was added into the solution 2, and the mixed solution was stirred while heating to 80° C. and then kept at 80° C. for two hours. After the reaction was finished, toluene was removed by concentrating in vacuum to obtain compound I-11.

NMR characterization of compound I-11: $^1$H NMR (500 MHz, CDCl$_3$), δ 10.58 (1H), 5.21 (1H), 4.91 (1H), 3.18 (4H), 3.02 (1H), 2.87 (2H), 2.46 (4H), 2.21 (2H), 1.94 (2H), 1.55 (2H), 1.54 (2H), 1.52 (4H), 1.44 (4H), 1.33 (2H), 1.30 (2H), 1.30 (2H), 1.29 (2H), 1.29 (4H), 1.29 (4H), 1.26 (20H), 1.26 (40H), 1.25 (2H), 1.25 (2H), 0.88 (3H).

$^{13}$C NMR (500 MHz, CDCl$_3$), δ 178.4, 170.8, 130.9, 128.8, 83.7 (2C), 68.6 (2C), 50.0 (2C), 38.0, 34.8, 34.0, 31.9, 29.9, 29.9, 29.7, 29.7, 29.6 (8C), 29.6 (16C), 29.3, 29.3 (4C), 29.0, 29.0, 28.7 (6C), 27.3, 27.0 (2C), 24.7, 22.7, 18.4 (2C), 14.1.

Example 12

The present Example provides a compound I-12 represented by Formula I, which has a structural Formula as follows:

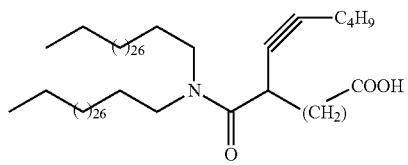

Compound I-12 was prepared by the synthesis route as follows:

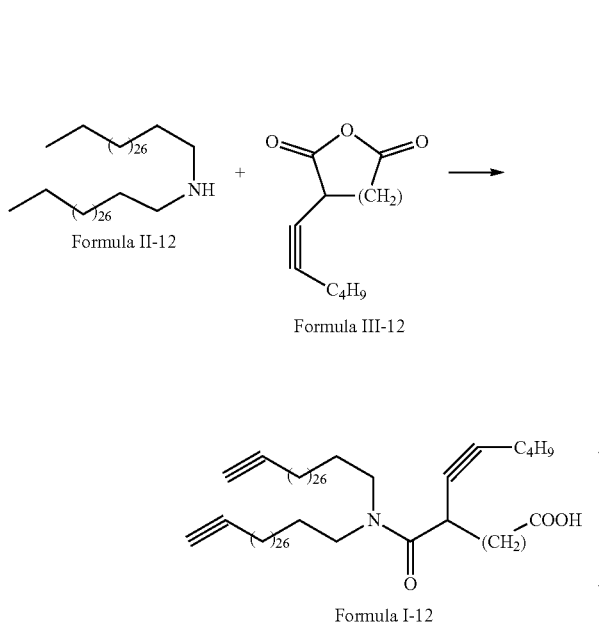

(1) N,N-dihydrocarbyl secondary amine represented by Formula II-12 (84.9 g, 0.10 mol) was dissolved in toluene (20 mL) to obtain solution 1; decenyl pimelic anhydride compound represented by Formula III-12 (18.0 g, 0.10 mol) was dissolved in toluene (30 mL) to obtain solution 2;

(2) the solution 1 was added into the solution 2, and the mixed solution was stirred while heating to 80° C. and then kept at 80° C. for two hours. After the reaction was finished, toluene was removed by concentrating in vacuum to obtain compound I-12.

NMR characterization of compound I-12: $^1$H NMR (500 MHz, CDCl$_3$), δ 10.88 (1H), 3.80 (1H), 3.18 (4H), 2.77 (2H), 1.96 (2H), 1.52 (2H), 1.44 (2H), 1.30 (2H), 1.29 (104H), 1.28 (4H), 0.89 (3H), 0.88 (6H).

$^{13}$C NMR (500 MHz, CDCl$_3$), δ 177.3, 173.6, 84.5, 78.6, 49.0 (2C), 35.2, 31.2, 29.0 (2C), 27.0, 22.4 (2C), 22.1 (52C), 21.5, 18.4, 14.1 (2C), 13.2.

Example 13

The present Example provides a compound I-13 represented by Formula I, which has a structural Formula as follows:

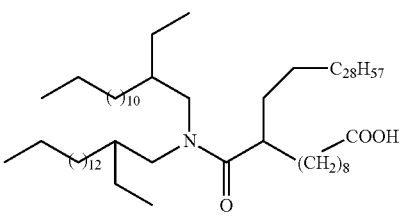

Compound I-13 was prepared by the synthesis route as follows:

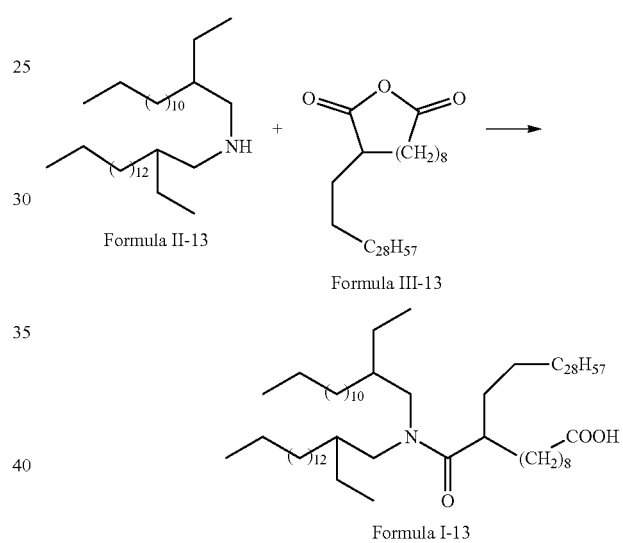

(1) N,N-dihydrocarbyl secondary amine represented by Formula II-13 (42.9 g, 0.10 mol) was dissolved in toluene (20 mL) to obtain solution 1; decenyl pimelic anhydride compound represented by Formula III-13 (61.8 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hours.

After the reaction was finished, toluene was removed by concentrating in vacuum to obtain compound I-13.

NMR characterization of compound I-13: $^1$H NMR (500 MHz, CDCl$_3$), δ 10.58 (1H), 3.25 (4H), 2.27 (1H), 2.21 (2H), 1.92 (2H), 1.55 (4H), 1.54 (2H), 1.49 (4H), 1.33 (2H), 1.26 (96H), 1.25 (12H), 1.19 (4H), 0.99 (6H), 0.88 (9H).

$^{13}$C NMR (500 MHz, CDCl$_3$), δ 178.4, 173.8, 52.3 (2C), 42.4, 37.5 (2C), 34.0, 33.1, 33.0, 32.3 (2C), 31.9, 31.9 (2C), 29.9 (2C), 29.8 (2C), 29.7 (2C), 29.6 (36C), 29.4, 29.3 (2C), 29.2 (2C), 29.0, 27.1 (2C), 26.4 (2C), 24.7, 22.8, 22.7 (2C), 14.1 (2C), 14.0, 11.6 (2C).

Example 14

The present Example provides a compound I-14 represented by Formula I, which has a structural Formula as follows:

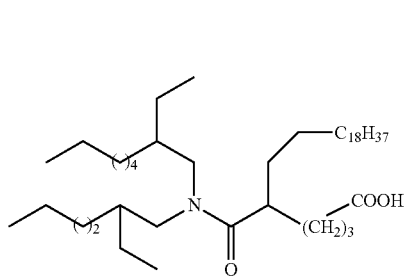

I-14

Compound I-14 was prepared by the synthesis route as follows:

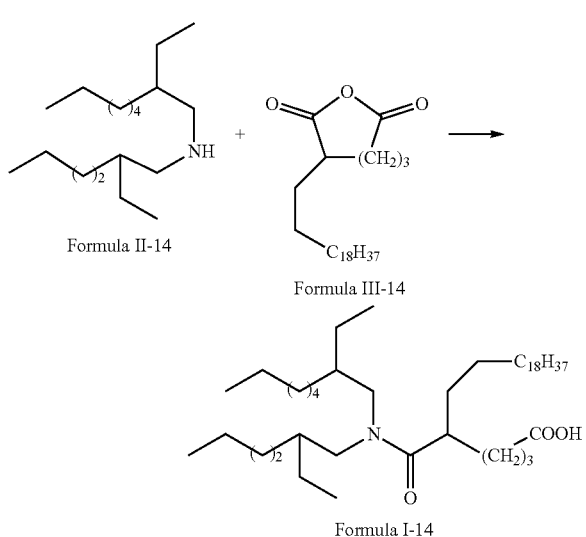

Formula II-14

Formula III-14

Formula I-14

(1) N,N-dihydrocarbyl secondary amine represented by Formula II-14 (27.0 g, 0.10 mol) was dissolved in toluene (20 mL) to obtain solution 1; decenyl pimelic anhydride compound represented by Formula III-14 (41.0 g, 0.10 mol) was dissolved in toluene (30 mL) to obtain solution 2;

(2) the solution 1 was added into the solution 2, and the mixed solution was stirred while heating to 80° C. and then kept at 80° C. for two hours. After the reaction was finished, toluene was removed by concentrating in vacuum to obtain compound I-14.

NMR characterization of compound I-13: $^1$H NMR (500 MHz, CDCl$_3$), δ 10.58 (1H), 3.25 (4H), 2.33 (2H), 2.27 (1H), 1.92 (2H), 1.55 (4H), 1.54 (2H), 1.49 (4H), 1.26 (22H), 1.25 (10H), 1.19 (4H), 0.99 (6H), 0.88 (9H).

$^{13}$C NMR (500 MHz, CDCl$_3$), δ 178.4, 173.8, 52.3 (2C), 42.1, 37.5 (2C), 33.6, 33.1, 32.3 (2C), 31.9, 31.8, 29.9, 29.8 (2C), 29.6 (13C), 29.5 (2C), 29.3, 29.2, 27.1, 26.4, 24.4, 22.8, 22.7 (2C), 14.2, 14.1 (2C), 11.6 (2C).

Example 15

The present Example provides a compound I-15 represented by Formula I, which has a structural Formula as follows:

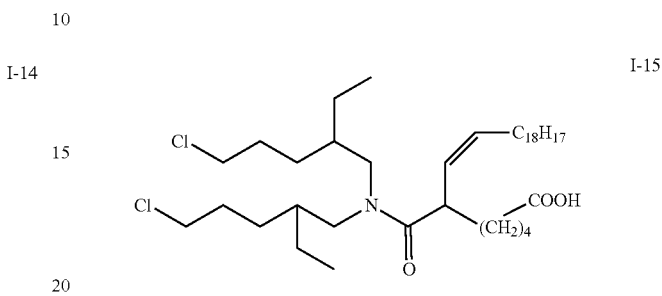

I-15

Compound I-15 was prepared by the synthesis route as follows:

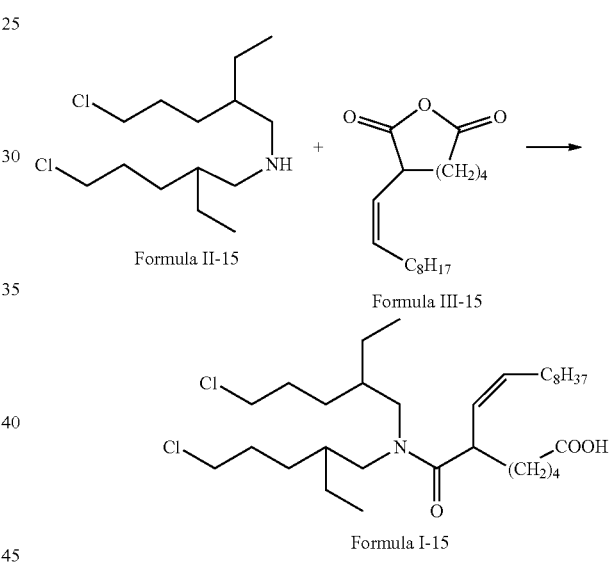

Formula II-15

Formula III-15

Formula I-15

(1) N,N-dihydrocarbyl secondary amine represented by Formula II-15 (28.3 g, 0.10 mol) was dissolved in toluene (20 mL) to obtain solution 1; decenyl pimelic anhydride compound represented by Formula III-15 (28.1 g, 0.10 mol) was dissolved in toluene (30 mL) to obtain solution 2;

(2) the solution 1 was added into the solution 2, and the mixed solution was stirred while heating to 80° C. and then kept at 80° C. for two hours. After the reaction was finished, toluene was removed by concentrating in vacuum to obtain compound I-15.

NMR characterization of compound I-15: $^1$H NMR (500 MHz, CDCl$_3$), δ 10.58 (1H), 5.21 (1H), 4.91 (1H), 3.74 (4H), 3.25 (4H), 3.02 (1H), 2.21 (2H), 1.94 (2H), 1.92 (2H), 1.55 (10H), 1.54 (2H), 1.33 (2H), 1.30 (2H), 1.29 (2H), 1.26 (6H), 1.25 (2H), 1.19 (4H), 0.99 (4H), 0.88 (3H).

$^{13}$C NMR (500 MHz, CDCl$_3$), δ 178.4, 170.8, 130.9, 128.8, 52.4 (2C), 45.0 (2C), 38.0, 36.7 (2C), 34.5, 34.0, 31.9, 30.5 (2C), 29.9, 29.8 (2C), 29.7, 29.6, 29.4 (2C), 29.3, 27.3, 25.9, 24.4, 22.7, 14.1, 11.6 (2C).

Comparative Example 1

Comparative Example 1 provides a compound I-d1 represented by Formula I-d1, which has a structural Formula as follows:

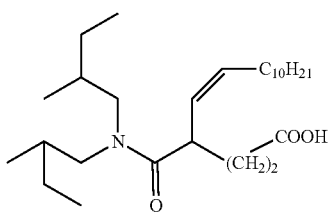

I-d1

Compound I-d1 was prepared by the synthesis route as follows:

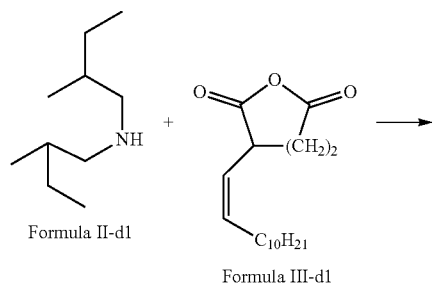

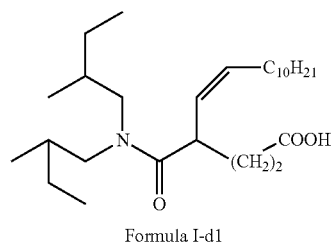

Formula I-d1

(1) N,N-dihydrocarbyl secondary amine represented by Formula I-d1 (15.7 g, 0.10 mol) was dissolved in toluene (20 mL) to obtain solution 1; anhydride compound represented by Formula III-d1 (28.2 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hours. After the reaction was finished, toluene was removed by concentrating in vacuum to obtain compound I-d1.

NMR characterization of compound I-d1: $^1$H NMR (500 MHz, CDCl$_3$), δ 10.58 (1H), 5.21 (1H), 4.91 (1H), 3.02 (1H), 3.00 (4H), 2.33 (2H), 2.12 (2H), 1.94 (2H), 1.84 (2H), 1.55 (4H), 1.33 (2H), 1.31 (2H), 1.30 (2H), 1.29 (2H), 1.26 (8H), 0.99 (6H), 0.93 (6H), 0.88 (3H).

$^{13}$C NMR (500 MHz, CDCl$_3$), δ 178.4, 170.8, 128.9, 128.3, 54.6 (2C), 37.4, 33.0 (2C), 32.9, 31.9, 29.9, 29.7, 29.7, 29.6, 29.6, 29.3, 28.2 (2C), 27.7, 27.3, 22.7, 18.1 (2C), 14.1, 11.3 (2C).

Comparative Example 2

Comparative Example 2 provides a compound I-d2 represented by Formula I-d2, which has a structural Formula as follows:

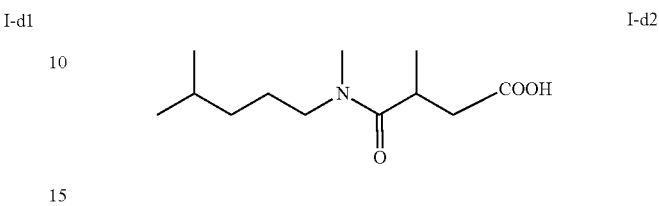

I-d2

Compound I-d2 was prepared by the synthesis route as follows:

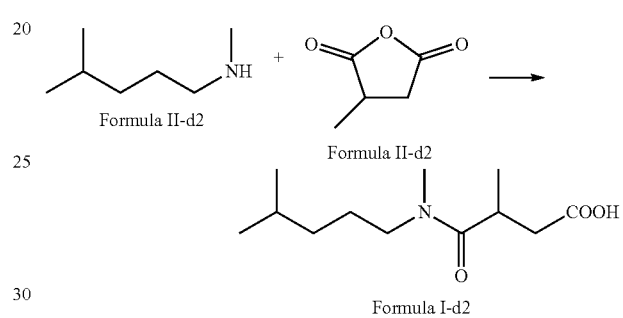

(1) N,N-dihydrocarbyl secondary amine represented by Formula I-d2 (11.5 g, 0.10 mol) was dissolved in toluene (20 mL) to obtain solution 1; anhydride compound represented by Formula III-d2 (11.4 g, 0.10 mol) was dissolved in toluene (30 mL) to obtain solution 2;

(2) the solution 1 was added into the solution 2, and the thus obtained mixture was stirred while heating to 80° C. and then kept at 80° C. for 2 hours. After the reaction was finished, toluene was removed by concentrating in vacuum to obtain compound I-d2.

NMR characterization of compound I-d2: $^1$H NMR (500 MHz, CDCl$_3$), δ 10.38 (1H), 3.18 (2H), 2.94 (3H), 2.86 (1H), 2.56 (2H), 1.52 (2H), 1.62 (1H), 1.19 (2H), 1.17 (3H), 0.91 (6H).

$^{13}$C NMR (500 MHz, CDCl$_3$), δ 177.3, 175.5, 52.4, 40.9, 37.0, 36.7, 36.3, 27.8, 24.7, 23.2 (2C), 17.2.

Comparative Example 3

Comparative Example 3 provides a compound I-d3 represented by Formula I-d3, which has a structural Formula as follows:

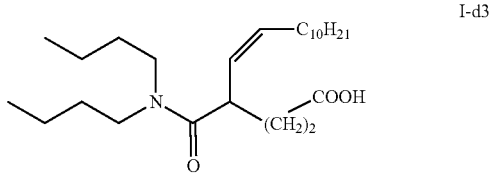

I-d3

Compound I-d3 was prepared by the synthesis route as follows:

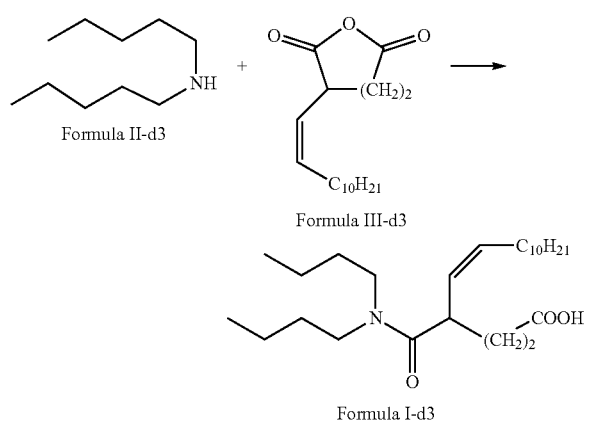

Formula II-d3

Formula III-d3

Formula I-d3

(1) N,N-dibutyl secondary amine represented by Formula I-d3 (12.9 g, 0.10 mol) was dissolved in toluene (20 mL) to obtain solution 1; anhydride compound represented by Formula III-d3 (28.1 g, 0.10 mol) was dissolved in toluene (30 mL) to obtain solution 2;

(2) the solution 1 was added into the solution 2, and the mixed solution was stirred while heating to 80° C. and then kept at 80° C. for two hours. After the reaction was finished, toluene was removed by concentrating in vacuum to obtain compound I-d3.

NMR characterization of compound I-d3: $^1$H NMR (500 MHz, CDCl$_3$), δ 10.58 (1H), 5.21 (1H), 4.91 (1H), 3.02 (1H), 3.18 (4H), 2.33 (2H), 1.94 (2H), 1.84 (2H), 1.52 (4H), 1.33 (2H), 1.31 (4H), 1.30 (4H), 1.29 (2H), 1.26 (8H), 0.99 (6H), 0.88 (3H).

$^{13}$C NMR (500 MHz, CDCl$_3$), δ 178.4, 170.8, 128.9, 128.3, 49.7 (2C), 37.4, 33.0, 30.0 (2C), 31.9, 29.9, 29.7, 29.7, 29.6, 29.6, 29.3, 27.7, 27.3, 20.1 (2C), 22.7, 14.1, 13.8 (2C).

Test Example 1

Test for Enrichment of Rare Earth Elements.

(1) the compounds prepared in the above Examples 1 to 15 and Comparative Examples 1 to 3 were used in weight of (6.6, 5.9, 6.6, 6.6, 6.1, 6.6, 6.6, 6.24, 6.97, 7.8, 11.66, 12.8, 13.01, 8.55, 7.3 and 5.53, 3.0, 5.3) g, respectively.

(2) The above extractants were respectively mixed with 0.96 mL of 10.8 mol/L sodium hydroxide aqueous solution, and saponified at 25° C. for 5 minutes to obtain viscous liquid of saponified extractants with saponification degree of 80%;

(3) at room temperature, the viscous liquid of saponified extractants were mixed with 2000 mL of ionic rare earth leaching solution for enrichment time of 0.5 hour. Ion-type rare earth leaching solution contained 15 rare earth elements including lanthanum, cerium, praseodymium, neodymium, samarium, europium, gadolinium, terbium, dysprosium, holmium, erbium, thulium, ytterbium, lutetium and yttrium, with a total molar concentration of 0.00636 mol/L. pH=6.0. The concentration of rare earth ions in the water phase before and after enrichment was measured, and the total enrichment ratio of rare earth ions E % was calculated;

The specific test results (total enrichment ratio of rare earth ions) were shown in Table 1:

TABLE 1

| Item | Example 1 | Example 2 | Example 3 | Example 4 | Example 5 | Example 6 |
|---|---|---|---|---|---|---|
| Total enrichment ratio E % | 97.5 | 98.4 | 98.5 | 97.5 | 98.9 | 98.6 |
| Item | Example 7 | Example 8 | Example 9 | Example 10 | Example 11 | Example 12 |
| Total enrichment ratio E % | 98.7 | 98.9 | 98.9 | 96.8 | 95.6 | 99.5 |
| Item | Example 13 | Example 14 | Example 15 | Comparative Example 1 | Comparative Example 2 | Comparative Example 3 |
| Total enrichment ratio E % | 98.5 | 96.7 | 97.7 | 94.5 | 92.7 | 93.6 |

It can be seen from the above table that the enrichment ratio of N,N-dihydrocarbyl amide carboxylic acid prepared according to in Examples 1 to 15 is above 95%, while the total enrichment ratio of N,N-dihydrocarbyl amide carboxylic acid in Comparative Examples 1 to 3 is below 95%. Therefore, the N,N-dihydrocarbyl amide carboxylic acid according to the present invention can be used as extractant to enrich rare earth elements from raw material containing low-concentration rare earth elements with better enrichment effect.

Test Example 2

Test for Separating Yttrium Ion (1) the compounds prepared in the above Examples 1 to 15 and Comparative Example 1 were respectively prepared into extractant solutions; to be specific, the extractants prepared in Examples 1 to 15 and Comparative Example 1 were taken in weight of 6.6 g, 5.9 g, 6.6 g, 6.6 g, 6.1 g, 6.6 g, 6.6 g, 6.24 g, 6.97 g, 7.8 g, 11.66 g, 12.8 g, 13.01 g, 8.55 g, 7.3 g and 5.53 g, 3.0 g, 5.3 g, respectively; toluene was taken in weight of 18.4 g, 19.1 g, 18.4 g, 18.4 g, 18.9 g, 18.4 g, 18.4 g, 18.76 g, 18.03 g, 17.2 g, 13.34 g, 12.2 g, 12.99 g, 16.45 g, 17.7 g and 19.47 g, 22.0 g, 19.7 g, respectively; the above two components were mixed to obtain extractant solutions with concentration of 0.52 mol/L;

(2) thus obtained extractant solutions were respectively mixed with 0.96 mL of 10.8 mol/L sodium hydroxide aqueous solution, and saponified at 25° C. for 5 min to obtain saponified extractant solutions with saponification degree of 80%;

(3) at room temperature, 25 mL of the saponified extractant solutions and 25 mL of mixed rare earth solution were mixed and extracted for 0.5 h. The mixed rare earth solution contained 15 rare earth elements including lanthanum, cerium, praseodymium, neodymium, samarium, europium, gadolinium, terbium, dysprosium, holmium, erbium, thulium, ytterbium, lutetium and yttrium, with a concentration of 0.020 mol/L for each element. The concentrations of rare earth ions in aqueous phase before and after extraction were measured, and the relative separation coefficient $\beta_{Ln/Y}$ of each rare earth ion (Ln) relative to yttrium ion (Y) was calculated;

The specific test results (relative separation coefficient $\beta_{Ln/Y}$ of rare earth ions (Ln) relative to yttrium ions (Y)) were shown in Table 2.

Specific test results (the extractant loss rate in hydrochloric acid medium and liquid alkali medium) were shown in Table 3 below:

TABLE 3

| Item | in hydrochloric acid medium, extractant loss rate (%) | in liquid alkali medium, extractant loss rate (%) |
|---|---|---|
| Example 1 | 0.04 | 0.06 |
| Example 2 | 0.04 | 0.06 |
| Example 3 | 0.04 | 0.06 |
| Example 4 | 0.04 | 0.06 |
| Example 5 | 0.04 | 0.06 |
| Example 6 | 0.05 | 0.07 |
| Example 7 | 0.04 | 0.06 |
| Example 8 | 0.05 | 0.07 |
| Example 9 | 0.04 | 0.06 |
| Example 10 | 0.04 | 0.06 |
| Example 11 | 0.04 | 0.06 |

TABLE 2

| $\beta_{Ln/Y}$ | La/Y | Ce/Y | Pr/Y | Nd/Y | Sm/Y | Eu/Y | Gd/Y | Tb/Y | Dy/Y | Ho/Y | Er/Y | Tm/Y | Yb/Y | Lu/Y |
|---|---|---|---|---|---|---|---|---|---|---|---|---|---|---|
| Example 1 | 1.10 | 1.29 | 1.72 | 2.06 | 3.01 | 2.96 | 2.18 | 2.26 | 2.30 | 2.39 | 2.48 | 2.59 | 2.88 | 3.15 |
| Example 2 | 1.12 | 1.27 | 1.72 | 2.06 | 3.01 | 2.96 | 2.18 | 2.27 | 2.29 | 2.37 | 2.47 | 2.57 | 2.85 | 3.10 |
| Example 3 | 1.11 | 1.30 | 1.72 | 2.06 | 3.01 | 2.96 | 2.18 | 2.26 | 2.29 | 2.37 | 2.46 | 2.57 | 2.85 | 3.14 |
| Example 4 | 1.09 | 1.29 | 1.72 | 2.06 | 3.01 | 2.96 | 2.18 | 2.26 | 2.3 | 2.39 | 2.48 | 2.59 | 2.88 | 3.14 |
| Example 5 | 1.12 | 1.27 | 1.72 | 2.06 | 3.01 | 2.96 | 2.18 | 2.27 | 2.29 | 2.37 | 2.47 | 2.57 | 2.85 | 3.11 |
| Example 6 | 1.13 | 1.30 | 1.73 | 2.07 | 3.02 | 2.98 | 2.20 | 2.28 | 2.30 | 2.39 | 2.49 | 2.62 | 2.9 | 3.17 |
| Example 7 | 1.14 | 1.31 | 1.73 | 2.07 | 3.02 | 2.98 | 2.20 | 2.28 | 2.30 | 2.39 | 2.50 | 2.62 | 2.91 | 3.19 |
| Example 8 | 1.10 | 1.29 | 1.72 | 2.06 | 3.01 | 2.96 | 2.18 | 2.26 | 2.30 | 2.39 | 2.48 | 2.59 | 2.88 | 3.15 |
| Example 9 | 1.21 | 1.32 | 1.82 | 2.08 | 3.02 | 2.97 | 2.19 | 2.28 | 2.32 | 2.42 | 2.51 | 2.61 | 2.97 | 3.35 |
| Example 10 | 1.10 | 1.23 | 1.77 | 2.09 | 3.06 | 2.99 | 2.28 | 2.29 | 2.33 | 2.42 | 2.50 | 2.56 | 2.83 | 3.11 |
| Example 11 | 1.13 | 1.32 | 1.80 | 2.04 | 3.05 | 2.98 | 2.12 | 2.23 | 2.32 | 2.41 | 2.48 | 2.54 | 2.86 | 3.13 |
| Example 12 | 1.08 | 1.33 | 1.73 | 2.07 | 3.04 | 3.00 | 2.13 | 2.23 | 2.35 | 2.42 | 2.49 | 2.51 | 2.89 | 3.18 |
| Example 13 | 1.16 | 1.30 | 1.74 | 2.09 | 3.03 | 2.93 | 2.12 | 2.29 | 2.30 | 2.40 | 2.43 | 2.59 | 2.88 | 3.19 |
| Example 14 | 1.14 | 1.39 | 1.77 | 2.08 | 3.09 | 2.99 | 2.23 | 2.26 | 2.33 | 2.42 | 2.51 | 2.66 | 2.91 | 3.27 |
| Example 15 | 1.28 | 1.35 | 1.75 | 2.05 | 3.12 | 3.02 | 2.24 | 2.27 | 2.32 | 2.43 | 2.54 | 2.68 | 2.91 | 3.29 |
| Comparative Example 1 | 0.98 | 1.22 | 1.60 | 1.84 | 2.95 | 2.93 | 2.15 | 2.22 | 2.21 | 2.26 | 2.32 | 2.49 | 2.83 | 3.07 |
| Comparative Example 2 | 0.88 | 1.05 | 1.48 | 1.79 | 2.91 | 2.92 | 2.10 | 2.15 | 2.06 | 2.04 | 2.17 | 2.50 | 2.77 | 3.06 |
| Comparative Example 3 | 1.03 | 1.21 | 1.55 | 1.78 | 2.92 | 2.93 | 2.14 | 2.21 | 2.17 | 2.19 | 2.25 | 2.47 | 2.82 | 3.08 |

It can be seen from table 2 that the separation coefficient ($\beta_{Ln/Y}$) of N,N-dihydrocarbyl amide carboxylic acids of Examples 1 to 15 for each rare earth element is higher than that of Comparative Examples 1 to 3. The N,N-dihydrocarbyl amide carboxylic acids defined by the present invention can better separate and purify yttrium element from mixed rare earth raw materials.

Test Example 3

Stability Test

The stability of compound I-1 prepared in the above Example 1 was tested by the following procedure: compound I-1 was prepared into an extractant solution by dissolving 50.9 g of compound I-1 in 100 mL of toluene to prepare an extractant solution with a concentration of 1.0 mol/l; 50 mL of extractant solution and 50 mL of hydrochloric acid solution with concentration of 6 mol/L were mixed and stirred for 15 days, and another 50 mL of extractant solution and 50 mL of sodium hydroxide solution with concentration of 6 mol/L were mixed and stirred for 15 days, and then the extractant loss rate in both was tested by NMR. The stability of compounds according to Examples 2 to 15 and Comparative Examples was tested in the same manner as that of compound I-1;

TABLE 3-continued

| Item | in hydrochloric acid medium, extractant loss rate (%) | in liquid alkali medium, extractant loss rate (%) |
|---|---|---|
| Example 12 | 0.02 | 0.05 |
| Example 13 | 0.04 | 0.07 |
| Example 14 | 0.03 | 0.06 |
| Example 15 | 0.04 | 0.07 |
| Comparative Example 1 | 0.07 | 0.08 |
| Comparative Example 2 | 0.07 | 0.09 |
| Comparative Example 3 | 0.06 | 0.08 |

It can be seen from the test data in table 3 that the loss rate of N,N-dihydrocarbyl amide carboxylic acid in hydrochloric acid medium was below 0.05%; and the loss rate in caustic soda liquid medium was below 0.07%. Therefore, the N,N-dihydrocarbyl amide carboxylic acids prepared by the present invention have excellent chemical stability and can withstand strong acid and strong alkali without decomposition.

The applicant declares that the N,N-dihydrocarbyl amide carboxylic acid and its preparation method and use according to the present invention are illustrated by the above Examples, but the present invention is not limited to the above Examples, which does not mean that the present invention should be implemented only by relying on the above Examples. It should be understood to those skilled in the art that any improvement to the present invention, equivalent replacement of raw materials, addition of auxiliary components, selection of specific embodiments, etc., shall fall within the scope of protection and disclosure of the present invention.

The invention claimed is:

1. An N,N-dihydrocarbyl amide carboxylic acid with a structure represented by Formula I:

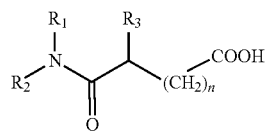

Formula I wherein, $R_1$ and $R_2$ are each independently a linear or branched, saturated or unsaturated, and unsubstituted C6 or more hydrocarbyl;
$R_3$ is a linear or branched, saturated or unsaturated, and unsubstituted C6 or more hydrocarbyl;
n is a natural number from 1 to 10.

2. The N,N-dihydrocarbyl amide carboxylic acid according to claim 1, wherein, $R_1$ and $R_2$ are each independently a linear or branched, saturated or unsaturated, and unsubstituted C6-C30 hydrocarbyl.

3. The N,N-dihydrocarbyl amide carboxylic acid according to claim 1, wherein, $R_1$ and $R_2$ are each independently a branched, saturated or unsaturated, and unsubstituted C6 or more hydrocarbyl.

4. The N,N-dihydrocarbyl amide carboxylic acid according to claim 1, wherein, $R_1$ and $R_2$ are each independently a linear or branched and unsubstituted C6-C30 alkyl.

5. The N,N-dihydrocarbyl amide carboxylic acid according to claim 1, wherein n is a natural number from 1 to 6.

6. The N,N-dihydrocarbyl amide carboxylic acid according to claim 1, wherein $R_1$ and $R_2$ are independently

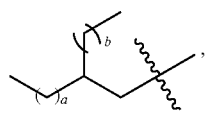

wherein 2≤a+b≤10, and represents a connecting site.

7. The N,N-dihydrocarbyl amide carboxylic acid according to claim 1, wherein $R_1$ and $R_2$ are independently any one selected from the group consisting of the following groups, wherein represents a connecting site,

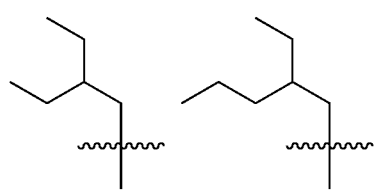

-continued

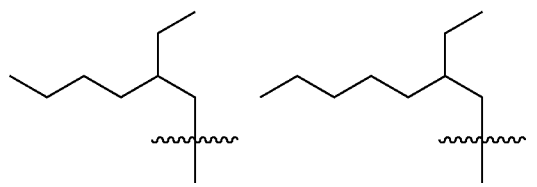

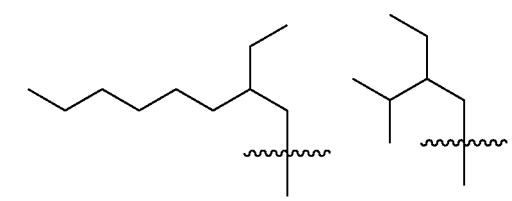

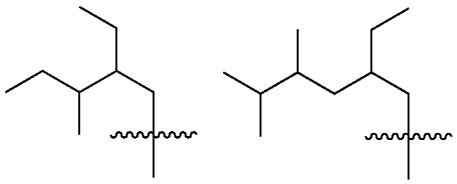

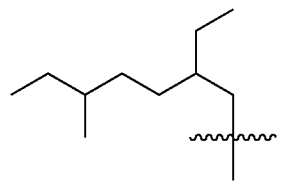

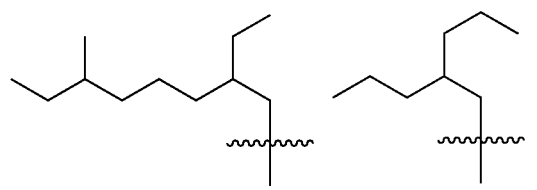

and

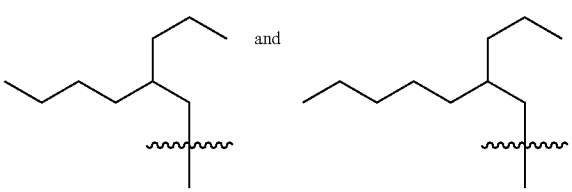

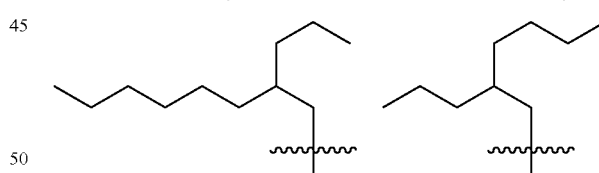

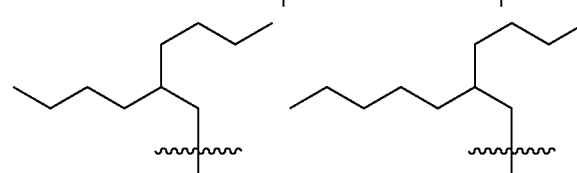

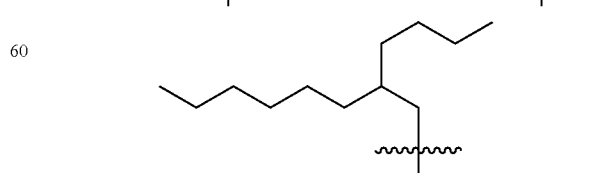

8. The N,N-dihydrocarbyl amide carboxylic acid according to claim 1, wherein, $R_3$ is selected from a linear or branched, saturated or unsaturated, and unsubstituted C6-C30 hydrocarbyl.

9. The N,N-dihydrocarbyl amide carboxylic acid according to claim 1, wherein, $R_3$ is selected from a linear or branched, unsaturated, and unsubstituted C6 or more hydrocarbyl.

10. The N,N-dihydrocarbyl amide carboxylic acid according to claim 1, wherein $R_3$ is any one selected from the group consisting of the following groups, wherein  represents a connecting site,

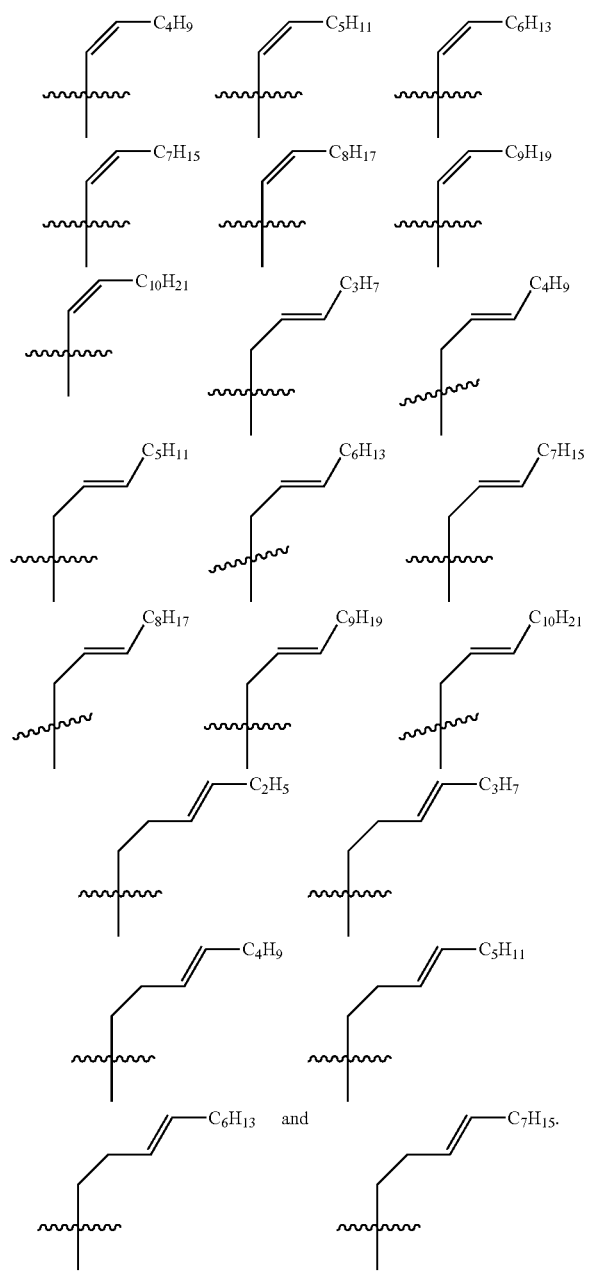

11. A method for preparing the N,N-dihydrocarbyl amide carboxylic acid according to claim 1 comprising a step of:

mixing and reacting an N,N-dihydrocarbyl secondary amine represented by Formula II and an anhydride compound represented by Formula III to obtain the N,N-dihydrocarbyl amide carboxylic acid represented by Formula I, as shown in the following Reaction Scheme:

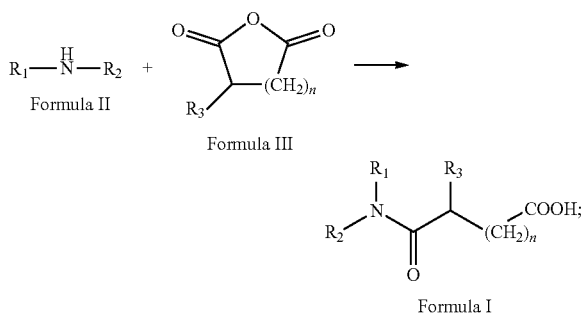

or mixing and reacting the N,N-dihydrocarbyl secondary amine represented by Formula II and a carboxylic acid-monoacyl chloride compound represented by Formula IV to obtain the N,N-dihydrocarbyl amide carboxylic acid represented by Formula I, as shown in the following Reaction Scheme:

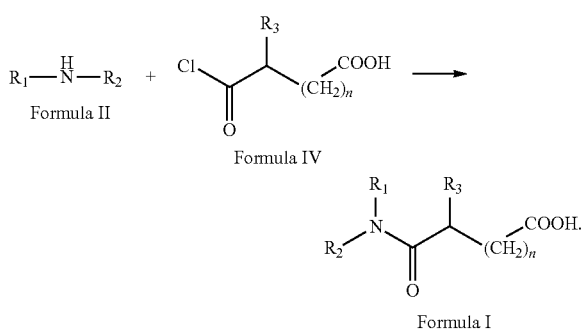

12. The method for preparing the N,N-dihydrocarbyl amide carboxylic acid according to claim 11, wherein a molar ratio between the N,N-dihydrocarbyl secondary amine represented by Formula II and the anhydride compound represented by Formula III is 1:(0.8-1.2); or
the molar ratio of the N,N-dihydrocarbyl secondary amine represented by Formula II and the carboxylic acid-mono acyl chloride compound represented by Formula IV is 1:(0.8-1.2).

13. The method for preparing the N,N-dihydrocarbyl amide carboxylic acid according to claim 11, wherein the N,N-dihydrocarbyl secondary amine represented by Formula II and the anhydride compound represented by Formula III are mixed and reacted at a temperature of 0° C. to 125° C. for 0.5 to 4 hours; or
the N,N-dihydrocarbyl secondary amine represented by Formula II and the carboxylic acid-mono acyl chloride compound represented by Formula IV are mixed and reacted at temperature of 0° C. to 125° C. for 0.5 to 4 hours.

14. The method for preparing the N,N-dihydrocarbyl amide carboxylic acid according to claim 11, wherein the N,N-dihydrocarbyl secondary amine represented by Formula II and the anhydride compound represented by Formula III are mixed and reacted in the absence of a solvent or in a solvent; or the N,N-dihydrocarbyl secondary amine represented by Formula II and the carboxylic acid-monoacyl chloride compound represented by Formula IV are mixed and reacted in the absence of a solvent or in a solvent; and when mixed in the solvent, the solvent is an inert solvent and selected from any one or a combination of at least two selected from the group consisting of hexane, dichloromethane, petroleum ether, toluene, xylene and kerosene.

15. The N,N-dihydrocarbyl amide carboxylic acid according to claim 1, wherein, $R_1$ and $R_2$ are each independently a linear or branched, saturated or unsaturated, and unsubstituted C6-C18 hydrocarbyl.

16. The N,N-dihydrocarbyl amide carboxylic acid according to claim 1, wherein, $R_1$ and $R_2$ are each independently a branched, saturated or unsaturated, and unsubstituted C6-C30 hydrocarbyl.

17. The N,N-dihydrocarbyl amide carboxylic acid according to claim 1, wherein, $R_1$ and $R_2$ are each independently a branched, saturated or unsaturated, and unsubstituted C6-C10 hydrocarbyl.

18. The N,N-dihydrocarbyl amide carboxylic acid according to claim 1, wherein, $R_1$ and $R_2$ are each independently a linear or branched and unsubstituted C6-C18 alkyl.

19. The N,N-dihydrocarbyl amide carboxylic acid according to claim 1, wherein, $R_1$ and $R_2$ are each independently a linear or branched and unsubstituted C6-C10 alkyl.

20. The N,N-dihydrocarbyl amide carboxylic acid according to claim 1, wherein, $R_3$ is selected from a linear C10 or more alkenyl.

21. The N,N-dihydrocarbyl amide carboxylic acid according to claim 1, wherein, $R_3$ is selected from a linear C10-C18 alkenyl.

* * * * *